(12) United States Patent
Hsia et al.

(10) Patent No.: US 7,229,629 B2
(45) Date of Patent: Jun. 12, 2007

(54) CARBOXYLATE-GATED-NITROXIDE (CGN) COMPOUNDS AND COMPOSITIONS AND METHODS OF USE THEREOF

(75) Inventors: Jen-Chang Hsia, Irvine, CA (US); Li Ma, Statesboro, GA (US)

(73) Assignee: SynZyme Technologies, LLC, Irvine, CA (US)

( * ) Notice: Subject to any disclaimer, the term of this patent is extended or adjusted under 35 U.S.C. 154(b) by 319 days.

(21) Appl. No.: 10/237,558

(22) Filed: Sep. 6, 2002

(65) Prior Publication Data

US 2003/0092764 A1 May 15, 2003

Related U.S. Application Data

(63) Continuation-in-part of application No. 09/948,505, filed on Sep. 6, 2001, now abandoned.

(51) Int. Cl.
A61K 9/00 (2006.01)
A61K 31/44 (2006.01)

(52) U.S. Cl. .................................. 424/400; 514/299

(58) Field of Classification Search ................. 424/400
See application file for complete search history.

(56) References Cited

U.S. PATENT DOCUMENTS

| | | | |
|---|---|---|---|
| 4,240,797 A * | 12/1980 | Hsia ............................. | 436/97 |
| 5,025,032 A | 6/1991 | Carney et al. | |
| 5,036,097 A | 7/1991 | Floyd et al. | |
| 5,250,672 A * | 10/1993 | Sadler et al. ............... | 536/17.3 |
| 5,352,442 A | 10/1994 | Proctor | |
| 5,405,874 A | 4/1995 | Carney et al. | |
| RE35,112 E | 12/1995 | Carney et al. | |
| 5,475,032 A | 12/1995 | Carney | |
| 5,488,145 A | 1/1996 | Carney | |
| RE35,213 E | 4/1996 | Floyd et al. | |
| 5,508,305 A | 4/1996 | Carney | |
| 5,578,617 A | 11/1996 | Carney et al. | |
| 5,591,710 A | 1/1997 | Hsia | |
| 5,622,994 A | 4/1997 | Carney et al. | |

(Continued)

FOREIGN PATENT DOCUMENTS

WO    WO 88/05044    7/1988

(Continued)

OTHER PUBLICATIONS

Kuppusamy et al, "Electron Paramagnetic Resonance Imaging of Rat Heart with Nitroxide and Polynitroxyl-Albumin," Biochemistry 1996, 35, 7051-7057.*
Golubev et al. ("Stobbe condensation with free iminoxyl radical"), Inst. Chem, Phys., Moscow, 1965, 4, 716-18.*

Primary Examiner—Michael Woodward
Assistant Examiner—Bethany Barham
(74) Attorney, Agent, or Firm—Karl Bozicevic; Bozicevic, Field & Francis LLP

(57) ABSTRACT

Carboxylic-gated-nitroxide (CGN) compounds and their esterified derivatives are discovered and disclosed as compositions and shown to have the potential in treating a variety of acute and chronic diseases and disorders resulting from reactive oxygen species (ROS) injury. Compositions for treating tissue damage from ROS injury containing CGN, or active derivatives thereof, in a suitable pharmaceutical, cosmetic, and diagnostic formulations are described.

8 Claims, 27 Drawing Sheets

U.S. PATENT DOCUMENTS

| | | | |
|---|---|---|---|
| 5,679,691 A | 10/1997 | Ribier et al. | |
| 5,681,965 A | 10/1997 | Carney et al. | |
| 5,714,482 A | 2/1998 | Proctor | |
| 5,714,510 A | 2/1998 | Proctor | |
| 5,716,947 A | 2/1998 | Proctor | |
| 5,723,502 A | 3/1998 | Proctor | |
| 5,725,839 A | 3/1998 | Hsia | |
| 5,728,714 A | 3/1998 | Proctor | |
| 5,741,893 A | 4/1998 | Hsia | |
| 5,767,089 A | 6/1998 | Hsia | |
| 5,780,257 A | 7/1998 | Aoyama et al. | |
| 5,780,510 A | 7/1998 | Carney | |
| 5,789,376 A | 8/1998 | Hsia | |
| 5,804,561 A | 9/1998 | Hsia | |
| 5,807,831 A | 9/1998 | Hsia | |
| 5,811,005 A | 9/1998 | Hsia | |
| 5,817,632 A | 10/1998 | Hsia | |
| 5,824,781 A | 10/1998 | Hsia | |
| 5,840,701 A | 11/1998 | Hsia | |
| 5,840,734 A | 11/1998 | Bernstein | |
| 5,981,548 A | 11/1999 | Paolini et al. | |
| 6,002,001 A | 12/1999 | Carney et al. | |
| 6,048,967 A | 4/2000 | Hsia | |
| 6,017,315 A | 8/2000 | Carney et al. | |
| 6,197,826 B1 | 3/2001 | Waterbury et al. | |
| 6,235,931 B1 | 5/2001 | Wang et al. | |
| 6,239,145 B1 | 5/2001 | Utsumi et al. | |
| 6,342,523 B1 | 1/2002 | Waterbury et al. | |
| 6,403,627 B1 | 6/2002 | Carney et al. | |
| 6,495,720 B1 | 12/2002 | Couturier et al. | |
| 6,552,040 B1 * | 4/2003 | Bernstein | 514/315 |
| 2002/0091266 A1 | 7/2002 | Anggard et al. | |

FOREIGN PATENT DOCUMENTS

| | | | |
|---|---|---|---|
| WO | WO 97/41826 | 11/1997 | |
| WO | WO 99/37616 | 7/1999 | |
| WO | WO 00/61544 | 10/2000 | |
| WO | WO 00/78316 | 12/2000 | |
| WO | WO 03/030860 | * | 4/2003 |

* cited by examiner

Figure 14. *Representative chromatographic traces of a mixture of DETOPS, ETOPS and TOPS is show.*

Figure 15. *Distribution of DETOPS between water and octanol before and after hydrolysis.*

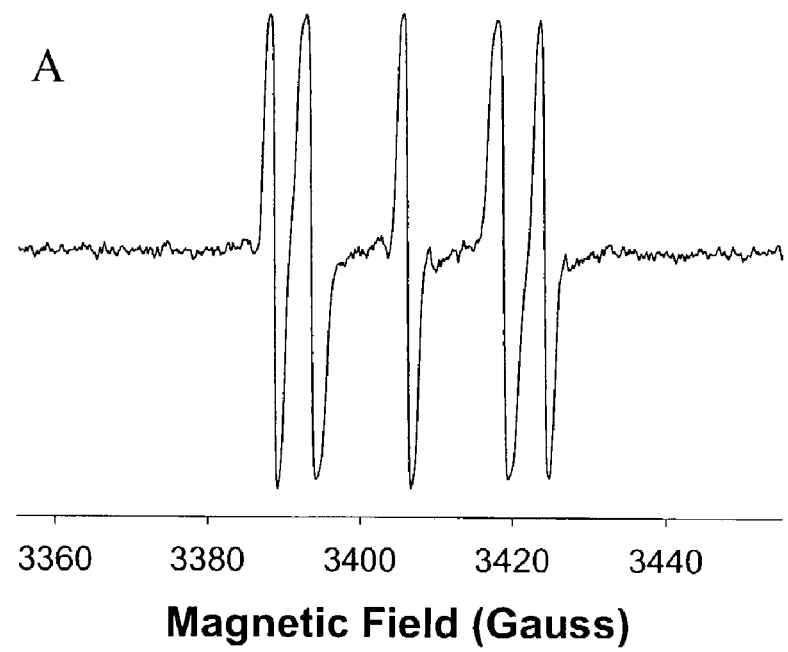
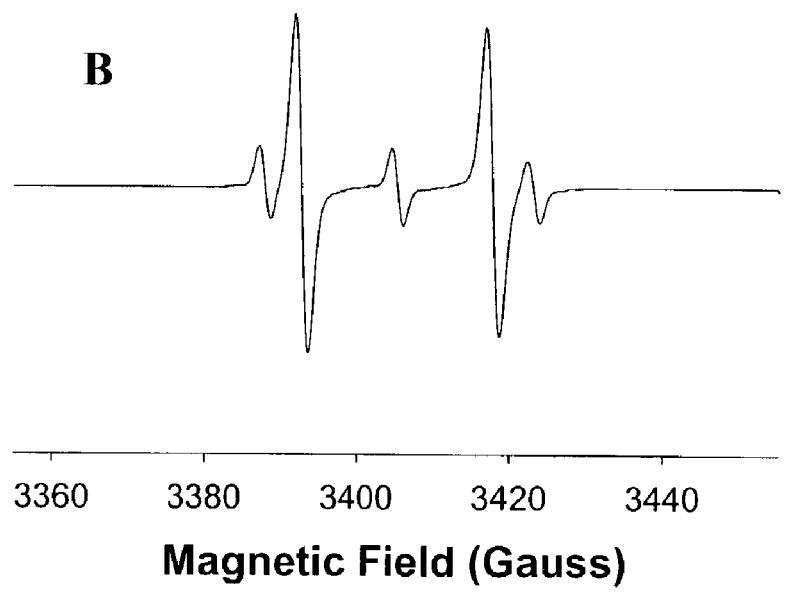
Figure 17

The plasma half-life measured in mouse-tail when $^{15}$NTempol co-injected i.p. with $^{14}$N E-TOPS by determined by EPR The plasma half-life measured in mouse-tail when $^{15}$N-Tempol co-injected i.v. with $^{14}$N-E-TOPS by determined by EPR The plasma half-life measured in mouse-tail when $^{15}$N-Tempol co-injected i.m. with $^{14}$N-E-TOPS by determined by EPR The plasma half-life measured in mouse-tail when $^{15}$N-Tempol co-injected orally with $^{14}$N-E-TOPS by determined by EPR DE-TOPS treated group On day $8^{th}$ Control jelly treated group On day $8^{th}$

Histopathology Observation in Mouse UVB Radiation Model of Post DermoZyme Treatment A: Epidermis thickening
(normal is scaling 1)
B: Dermis thickening
(normal is scaling 1)
C: Hemorrhage
(normal is scaling 0)
D: Inflammation
(normal is scaling 0)

$P < 0.0001$ in all groups (t-test)
N (animal) = 4 per group
N (sample) = 8 per animal

CARBOXYLATE-GATED-NITROXIDE (CGN) COMPOUNDS AND COMPOSITIONS AND METHODS OF USE THEREOF

CROSS-REFERENCE

This application is a continuation-in-part of our earlier filed U.S. patent application Ser. No. 09/948,505, filed Sep. 6, 2001, now abandoned, which application is incorporated herein by reference and to which application is claimed priority under 35 U.S.C. §120.

FIELD OF THE INVENTION

This invention relates to the treatment and prevention of chronic and acute diseases and disorders originated from oxidative stress. Novel compounds, compositions and their methods of use also relate to the field of therapeutic and diagnostic pharmaceuticals.

BACKGROUND OF THE INVENTION

Many acute and chronic diseases and disorders are attributable to the injuries from endogenously and exogenously generated reactive oxygen species ("ROS"). ROS injuries occur when the normal detoxifying capability of antioxidant enzymes and vitamins are overwhelmed. Supplements containing recombinant antioxidant enzymes and vitamins treating ROS injuries have revealed some advantages and limitations. Nitric oxide (NO•) and superoxide ($O_2$•$^-$) are both physiological gaseous free radicals which alone or in combination are capable of initiating the ROS cascade and injuries. Onging drug development programs target either supplementing or removing NO•. Using superoxide dismutase (SOD) as a model, an alternative drug development strategy is to target the removal of $O_2$•$^-$ and attenuation of follow-on ROS cascade. The latter programs involve mimicking the catalytic activities of SOD in a "metal-center" or a "metal-free" synthetic molecule such as chelated transition metal ion or nitroxide, respectively. The use of polynitroxylated "metal-center" (i.e. polynitroxyl hemoglobin) and "metal-free" (i.e. polynitroxyl albumin) blood proteins as vascular ROS injury protectants and imaging agents is described in patents such as U.S. Pat. Nos. 5,725,839; 5,741,893; 5,767,089; 5,804,561; 5,807,831; 5,817,632; 5,824,781; 5,840,701; 5,591,710; 5,789,376; 5,811,005; 6,048,967. However, it is generally accepted that no one approach can treat all ROS injuries. In fact, continued research efforts have been required to address new challenges not previously envisioned. The present invention shows the existence of a new synthetic analog of a "carboxylate-gated-nitroxide (CGN)" which is a center of activity.

The present invention also shows synthesis of CGN and its "metal-center" and "metal-free" novel compounds in esterified and non-esterified forms and their utility in targeted delivery to therapeutic sites of interest. In addition, conjugation via covalent linking and conjunctive use with existing drugs or targeting molecules increase their therapeutic applications.

SUMMARY OF THE INVENTION

Carboxylate-gated-nitroxide (CGN) compounds, their esterified derivatives compositions and methods of use for the treatment and prevention of diseases and disorders from ROS injuries are disclosed. Compositions of the invention are comprised of CGN and are useful for treating tissue exposed to undesirably high levels of reactive oxygen species (ROS). In addition to CGN, it is possible to use active derivatives thereof, in a suitable pharmaceutical, cosmetic, and diagnostic formulation for intravenous, i.p, i.m., oral, topical, nasal, pulmonary, or rectal administration. Examples of CGN and its derivatives include Esterified CGN, Esterified Dicarboxylic Amino acid CGN, and Esterified Carboxylic di-Amino acid CGN and their derivatives, including di-nitroxide, tri-nitroxide derivatives, or conjugates used alone or in combination with existing drugs or targeting molecules. Pharmaceutical formulations and routes of administration of the nitroxides are described. In particular, topical applications of compositions of the invention show how the targeted delivery of the CGN intracellularly is achieved through cellular esterase cleavage of hydropobic esterified CGN as a pro-drug to a hydrophilic CGN in its free acid form.

Nitroxide compounds of the invention comprise three molecular features which provide inventive characteristics. First, compounds of the invention comprise a first portion of a molecule comprising a nitrogen and an oxygen atom bound directly together and comprise an unpaired electron (•NO). Second, compounds of the invention comprise a second portion of the molecule which comprises at least two oxygen atoms, which second portion provides a negative charge, e.g. one, two, three or more carboxylic acid groups. The second portion may be structured so as to create the carboxylic acid groups after a given reaction e.g. the alkyl moieties of ester groups are removed. Third, compounds of the invention comprise a linking group positioned between the first and second portions which linking group allows the negative charge effect of the second portion to "bend toward" the first position and thereby aid in maintaining the stability of the (•NO) portion in a range of environments in a human body.

The compositions and routes of administration of the CGN are described in topical applications to show how the targeted delivery of the CGN intracellularly is achieved through the cellular esterase cleavage of hydropobic esterified CGN as a pro-drug to a hydrophilic CGN in its free acid form. Improvement of biological half-life and intracellular delivery over 4-hydroxyl-2,2,6,6-tetramethyl-piperidine-1-oxyl, a prior art compound, is definitively demonstrated using nitrogen stable isotopes of the two nitroxides and their co-administration (aerosol, rectal, and oral) distribution, metabolism and elimination studies as detected by electron paramagnetic resonance spectroscopy. This invention shows that esterase hydrolyzed esterified CGN provide their carboxylic acid moiety as the "gate" which protects the in vivo stability of the molecule without affecting catalytic activity. Examples of topical, i.v., oral, and pulmonary administration presented include the selected derivatives of CGN. The examples of efficacies of CGN in the prevention of acute and chronic skin lesions induced by UVB when applied pre- and post radiation are presented.

DESCRIPTION OF THE FIGURES

FIGS. 17(A and B) shows the hydrolysis of $^{14}N$-$^{15}N$TE-TOPS to two mono radical in vitro and in vivo.

DETAILED DESCRIPTION OF THE INVENTION

Figure 1:
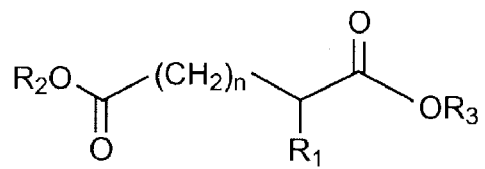
FIG. 1 shows the generic structural formula of esterified carboxylate-gated nitroxide (CGN) and their derivatives.

Before the present compounds, formulations and uses are described, it is to be understood that this invention is not limited to particular structures, formulae and uses described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a nitroxide" includes a plurality of such compounds or functional groups cells and reference to "the formulation" includes reference to one or more formulations and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Further, compounds of the invention may be structured so that it reacts with a biological organism it is provided to in a manner with changes the structure of the compound thereby enhancing cite directed delivery of the compound to a desired location.

Compounds of the invention are specifically designed for increased diagnostic and therapeutic utility when applied in a biological context where intracellular retention is important and where hydrophobic barriers such as skin, stratum corneum, or other such membranes are selectively permeable. These compositions are particularly useful when delivered to esterase-containing cells. These compositions may be used to alleviate the toxic effects of free radicals in a living organism that result from exposure to chemical agents and toxins, as well as sun, UV, or other forms of ionizing radiation. Specialized methods and formulations also enable the compounds of the invention to diagnose and treat a wide variety of physiological conditions, and to analyze in vivo reactions with imaging techniques that measure nitroxides and their reactivity. The invention also relates to novel nitroxide compositions that permit targeting or compartmentalization of a therapeutic dose of nitroxide within a localized area, particularly penetration and retention within an intra-dermal interface in the skin.

Compounds of the invention may be defined by the structural formulae as shown in FIGS. 1–13. These compounds can be formulated in any desired manner e.g. to create any desired pharmaceutically effective formulation. The compound may be mixed with, dissolved and/or suspended in a pharmaceutically acceptable carrier. The carrier may be chosen based on the intended use. For example, creams, gels and lotions may be used for topical applications to the skin. Saline solutions may be used as injectables.

The compounds and compositions of the invention may be applied in any desired manner. In general, compounds are formulated into compositions suitable for a particular type of administration e.g. lotions applied to human skin, aqueous/ethanol formulation to gargle in the mouth and upper throat, an aqueous saline solution for injection.

Invention in General

There are many aspects to the invention including compounds, formulations comprised of the compounds in a suitable carrier, and methods of treatment. The compounds are structured to provide the antioxidation effect of CGN to a biological organism (e.g. human) and to provide that effect over a sufficiently long period so as to obtain a desired therapeutic result. CGNs of the invention are structured in a manner such that the NO group is "gated" by carboxylate within the same molecule so that its redox modulation function is maintained over a longer period of time in vivo.

The NO group of CGN may be symmetrically or asymmetrically positioned relative to 2 carboxylate groups.

Compounds of the invention (see FIGS. 1–13) can be combined into a wide range of formulations for a range of different treatments. The treatment is generally a modulation of a biochemical reaction or more specifically a lessening of oxidation reactions as described further here. The modulation effects obtained are generally greater than the antioxidant effects of vitamins such as vitamin C and generally less than the effects of endogenous catalysts. The need for modulating oxidation reactions is often created by the human body's overreaction to infections as described generally below.

The blood is made up of plasma, red blood cells and white blood cells. The red blood cells allow for oxygen transportation and the white blood cell provide a defense against infection. White blood cells include leukocytes which include two types—lymphocytes and monocytes. White blood cells also include granulocytes which are divided into three types—basophils, eosinphils and neutrophils.

The neutrophils are the most abundant of the white blood cells and of particular interest as regards the present invention. The neutrophils squeeze through the capillary walls to find infected tissue or what may be mistaken as infected tissue which has been subjected to trauma. Neutrophils are released from bone marrow, circulate and are directed toward infection and inflammation by chemotaxis which moves cells toward a higher concentration of a given chemical. Once a neutrophil finds a foreign particle or a bacteria the neutrophil engulfs it, releases enzymes, hydrogen peroxide and other chemicals from its granules and oxidizes it e.g. kills the bacteria. Pus at a cite of infection is dead neutrophils and other cellular debris. Although this process is healthy in fighting infection, the body generally over reacts and causes additional inflammation due to excessive oxidation see U.S. Pat. No. 5,211,937 and in particular FIG. 5 thereof.

Compounds of the invention can decrease the rate of and/or overall amount of the oxidation and thereby reduce inflammation. A CGN compound of the invention may provide advantages over conventional nitroxides for example 4-hydroxy-2,2,6,6-tetramethylpiperidine-1-oxyl (Tempoll) such as the following:

1) Target delivery: CGN ester penetrates the stratum corneum and is preferentially taken up by viable skin cells following topical application. Upon entering the cell, the ester bonds of the prodrug are cleaved by intracellular esterases, converting the CGN to its free acid form and making it much less membrane permeable. This in vivo enzymatic conversion effectively compartmentalizes the CGN inside the esterase containing skin cell.

2) In vivo gating function: In its hydrolyzed free acid state, the carboxylate serving as the "gate", will protect or safeguard the intracellular catalytic activities of nitroxide.

3) In vivo safety: Acute toxicity ($LD_{50}$) of CGN, unlike Tempol ($LD_{50}$=375 mg/kg), was not detectable at 2 g/kg.

In short, the invention discloses CGN with a intramolecular carboxylate moiety that "safeguard" the in vivo reduction of its nitroxide moiety without affecting its catalytic activities.

The present invention discloses compounds, formulations and methods of use of carboxylate-gated nitroxide (CGN) for the prevention and treatment of diseases or injuries arising from reactive oxygen spices (ROS). Compounds, formulations and methods of the invention may be used alone or in combination with compounds disclosed in any of U.S. Pat. Nos. 5,725,839; 5,741,893; 5,767,089; 5,804,561;

5,807,831; 5,817,632; 5,824,781; 5,840,701; 5,591,710; 5,789,376; 5,811,005; 6,048,967.

The present invention encompasses general classes of CGN including mono-function CGN and bi-function CGN. Mono-function CGN refers to its anti-ROS injury activity alone. Bi-function CGN refers to the addition of a $2^{nd}$ therapeutic activity from the conjugated existing drug moiety CGN not only provide "carboxylate-gate" effect but in its established form also targets delivery its intracellular anti-ROS activity. The in vivo targeted delivery and stability of CGN enhances its therapeutic index and diagnostic utility.

Stable mono- and bi-function CGN compounds including their esterified derivatives and precursors thereof alone and in formulations and the uses of such are disclosed. As mono-function CGN the oxidation/reduction activity and compartmentalization can be regulated by the esterification of the carboxylic acid group(s). Compounds of the invention comprise one or more carboxylate yields a "gate" function which in a "prodrug" (e.g. ester) form provide increased permeability of CGN across cell membranes and also result in an enhanced in vivo half-life. The CGN may be modified with existing drugs via ester or amide groups to form bi-function CGN.

Compositions for treating tissue damage from ROS injury contain CGN, its esters or active drug derivatives thereof, in a suitable pharmaceutical, cosmetic, and diagnostic formulation for intravenous, intra-peritoneal, intra-muscular, oral, topical, nasal, pulmonary, vaginal, transdermal or rectal administration.

Figure 2:
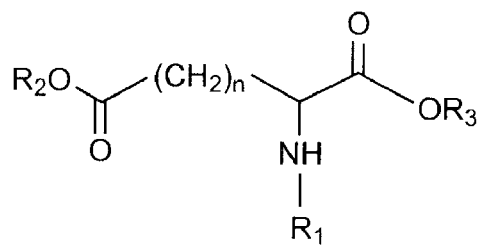
FIG. 2 shows the generic structure formulation of esterified di-carboxylic amino acid CGN
Figure 3:
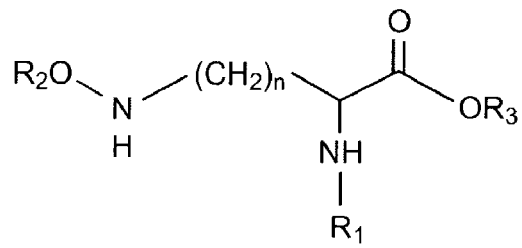
FIG. 3 shows the generic structure formulation of esterified carboxylic di-amino acid and their derivatives
Figure 4:
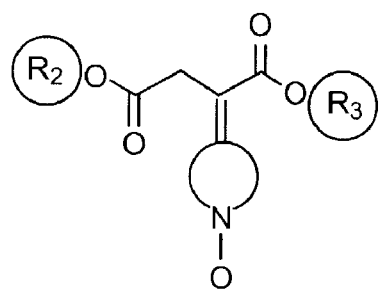
FIG. 4 shows the generic structures of the selected compounds, which are examplified in example section
Figure 5:
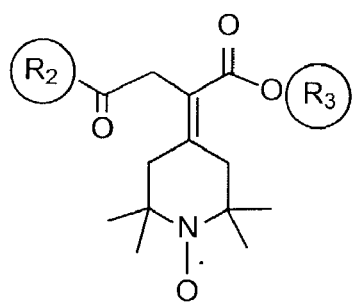
FIG. 5 shows the generic compound 2,2,6,6-tetramethyl-1-oxyl-piperidinene-4-succinate.
Figure 6:
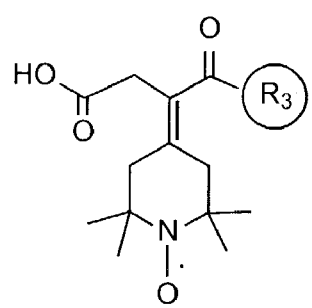
FIG. 6 shows the semi-generic structures of FIG. 5 with $R_2$ replaced by one hydroxyl (—H) group.

Compound Synthesis:

Three general structure formulae of CGN are shown in FIGS. 1, 2 and 3. Structure I is CGN described in FIG. 1. It is synthesized from the reaction of any keton or aldehyde nitroxide with esterified di-carboxylic acid. Structure II is mono-amino CGN described in FIG. 2. It is synthesized from the reaction of carboxyl or acetamido nitroxide with di-esterified dicarboxylic α-amino acid. Structure III is a di-amino acid CGN (see FIG. 3). It is synthesized from carboxyl or acetamido nitroxide with esterified and amidio di-amino acid, wherein esterified group is any compound with an OH function group including existing drug. In structure III the two amino groups serve to link a nitroxide and, optimally, other moieties with a carboxylic group. Thus, examples of CGN include esterified di-carboxylate CGN, esterified mono-amino acid CGN, and di-amino acid CGN and other derivatives, including di-nitroxide, tri-nitroxide derivatives, or conjugates used alone or in combination with existing drugs or targeting molecules.

The compositions and routes of administration of CGNs are described. Among many examples topical applications of compositions of the invention show how the targeted delivery of the CGN intracellularly is achieved through cellular esterase cleavage of hydrophobic esterified CGN as a pro-drug to a hydrophilic CGN in its free acid form. A second example of CGN such as E-TOPS has been tested for plasma half-life in co-administration as compared with a prior art nitroxide, Tempol. A prolonged half-life of E-TOPS over Tempol was observed when E-TOPS and Tempo were administrated (i.p, i.v., i.m., and oral). The third example of CGN such as DE-TOPS have been tested in hairless mouse model of UVB-induced skin damage.

Definitions

The term "nitroxide" is used herein to describe molecules comprising an oxygen and a nitrogen atom directly bound to each other. A nitroxide may be and electron donor or acceptor. Nitroxides may comprise stable nitroxyl free radicals including precursors (such as the N—H form), and derivatives thereof including their corresponding hydroxylamine derivative (N—OH) where the oxygen atoms are replaced with a hydroxyl group and exist in a hydrogen halide form. Nitroxides of the invention may be administered to a system, such as a human, and act to modulate oxidation and reduction reactions by donating or accepting an electron Stability of the unpaired electron of the nitroxide is provided at the nitrogen nucleus by two adjacent carbon atoms that are substituted with strong electron donor groups. With the partial negative charge on the oxygen of the N—O bond, the two adjacent carbon atoms together localize the unpaired electron on the nitrogen nucleus. Nitroxides generally may have either a heterocyclic or linear structure. A nitroxide of the invention may have one, two or more caryboxyl groups or groups such as ester groups which can be readily changed to carboxyl groups which groups aid in maintaining the free electron which allows the nictroxide to act as an electron donor. In an in vivo environment a nitroxide may react with a first superoxide to form oxoammonium (as an electron donor) and then react with a second superoxide to re-form the nitroxide (as an electron acceptor). If a nitroxide is reduced to a hydroxylamine it loses its ability to modulate reactions. By positioning the nitroxide between two carboxylic acid groups a "gating" effect is obtained, i.e. the nitroxide is protected and its ability to modulate reactions is maintained over a longer period of time in a greater range of in vivo environments as compared to a molecule lacking the carboxylic acid groups.

The terms "treat," "treatment" and the like are used herein to generally mean obtaining a desired pharmacological and/or physiological effect. A treatment is an approach for obtaining beneficial or desired clinical results which include but are not limited to decreasing undesirable effects of reactive oxygen species (ROS). The effect may be prophylactic in terms of completely or partially preventing a disease and/or symptom thereof and/or may be therapeutic in terms of a partial or complete cure of the disease and/or adverse effect attributed to the disease. In general, methods of the invention involve treating diseases generally associated with an inflammatory response and may be applied to a variety of different areas and in particular membrane surfaces including the skin, mucus membranes including those in the GI tract, nose, throat, mouth, vaginal cavity, ocular surfaces, as well as the surfaces of the lungs and the surfaces of the vascular system. "Treatment" as used herein covers any treatment of such a symptom or disease in a mammal, particularly a human, and includes:

(a) preventing or diagnosing the disease and/or symptoms in the subject which may be predisposed to the disease and/or symptom but has not yet been diagnosed as having it;

(b) inhibiting the disease, i.e. arresting it's development; and/or (c) relieving the disease and/or it's symptom, i.e. causing regression of the disease and/or the symptoms caused by the disease.

The invention is directed towards modulating the inflammatory response and in particular, modulating excessive oxidation. The inflammatory response and the accompanying excessive oxidation associated with such can be caused by a variety of physical traumas including subjecting the cells to all types of radiation including ultraviolet and nuclear radiation as well as blunt trauma. The treatment may be combined with other co-treatments such as using anti-inflammatory drugs or antibiotic drugs to modulate the inflammation and prevent infection.

Types of treatment which might be carried out using compounds and compositions of the invention including applying the compounds and/or compositions to the skin in order to treat sunburn before it occurs and/or treat the inflammatory response related to sunburn after the sunburn has taken place. Further, the patient's skin may be treated after and/or before the application of radiation used in the treatment of cancer or fluoroscopy. In a similar manner a patient may be allowed to gargle a mouthwash containing compounds of the invention in order to treat the adverse effect of radiation on the internal surfaces of the mouth and throat. Compounds of the invention may be applied directly to the bone marrow in order to provide for protection against excessive oxidation in the bone marrow. Compounds of the invention may be injected into a patient in order to modulate the inflammatory response and excessive oxidation in the vascular system. Compounds of the invention may be used in treatment when being included within a cosmetic formulation applied to the skin. Further, when the skin is subjected to cosmetic surgery and/or laser resurfacing compounds and formulations of the invention may be applied prior to the laser resurfacing and/or after the laser resurfacing in order to modulate the inflammatory response. These and other types of treatment will occur to those skilled in the art upon reading this disclosure.

The term "effective amount" is an amount sufficient to effect a beneficial or desired result including a clinical result, and as such an "effective amount" depends on the context in which it is being applied. An effective amount can be administered in one or more doses. An effective amount may be an amount sufficient to obtain treatment e.g. modulate undesirably high levels of reactive oxygen species.

"Comprising" and its cognates mean "including."

Molecular Characteristics

The physiological compartmentalization or site directed delivery of CGN pursuant to this invention can be achieved through several discrete chemical structures or molecular modifications. The molecules are designed pursuant to the criteria disclosed herein to provide the selected permeability and reactivity characteristics. Modified CGN compounds may be topically applied and targeted to specific cells e.g. viable cells of the epidermis. The membrane solubility of the nitroxide is altered by converting the CGN to the modified form as described herein. For example, ester groups are added making the molecule more lipid soluble. These groups are removed by reactions catalyzed by cellular esterase making CGN more water-soluble and less lipid soluble (e.g. less soluble in a human lipid by 1 log, 2 logs or 3 logs or more). Once the modified CGN has entered the cell, the ordinary intracellular hydrolysis mechanisms of endogenous esterase create derivatives of CGN, which have reduced membrane permeability. Thus, these compounds readily enter the cell (when lipid soluble), but resist leaving the cell (when more water soluble and less lipid soluble), and as a consequence, exhibit increased permeability for transmembrane entry into a viable cell. The decreased lipid solubility and increased water solubility also provides a decreased tendency of the nitroxide to seep out of the viable cells or tissue e.g. by ordinary physiological clearance processes. This feature yields selectable preferential compartmentalization in vivo and a sustained therapeutic or diagnostic potential.

As described herein, accumulation and sequestration or compartmentalization of CGN may be enhanced by esterification. Topical applications prefer a diester, which may be asymmetric, and where one esterified group is made more labile than the other. For example, the t-butyl esters of BE-TOPS will be more readily hydrolyzed than ethyl ester because it is more labile than ethyl ester. Hydrolysis of an asymmetric nitroxide comprising these two esters will thus first yield a less membrane permeable mono-carboxyl E-TOPS. The selection of the particular ester di-carboxylic acid derivatives, e.g., succinate, determines the compartmentalization and intracellular accumulation characteristics and thus may be tailored to be higher or lower for specific diagnostic or therapeutic indications. Likewise, preparation of di-esters of naturally occurring dicarboxylic amino acids (eg aspartate, glutamate)will permit increased accumulation and sequestration intracellularly and have an added advantage in that naturally occurring amino acids are well known in administration, distribution, metabolism and excretion (ADME) studies.

The CGN that can be employed in this invention are structurally diverse because the requisite property of the CGN is its ability to be esterified. Thus, CGNs in their monocarboxylic, dicarboxylic, or polycarboxylic state may be employed. Selected embodiments of the present invention have the following structures, although the invention contemplates derivatives, isomers, substitutions, polymers, and other routine chemical modifications that preserve the functionality herein.

Compounds of the invention include those encompassed by general structural formula I:

FIG. 1

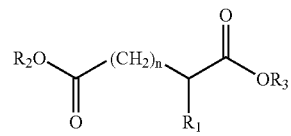

wherein $R_1$ is any nitroxide or more specifically any nitroxyl radical (NO) containing group with one unpaired electron localized around the nitrogen atom or more specifically a linear (straight or branched chain) or cyclic nitroxyl radical further comprising carbon and hydrogen atoms. An example of an $R_1$ is 2,2,6,6-tetramethyl-4-piperidene-1-oxyl;

wherein $R_2$ and $R_3$ are each independently hydrogen, alkyl, alkeynyl, aryl, aralkyl, akaryl or a nitroxide and in particular may independently be hydrogen, or ethyl, it should be noted that when $R_2$ and/or $R_3$ are H a carboxylic acid group is formed and the acid may be converted to a salt in the appropriate environment e.g. in a human body. Any salt may be formed and in particular Na and K salts may be formed; and wherein "n" is an integer of from 0 to 18 (e.g. 1–6 or 1–4) and in particular can be "1," "2" or "3."

In the structure I above the "$R_1$," group may be bound via a —NH— group to provide a structure of the invention as shown in formula II below:

FIG. 2

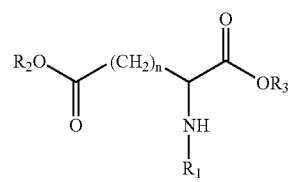

wherein the variables $R_1$, $R_2$, $R_3$ and n are as defined above and in particular "n" may be 1, 2 or 3. Further, n may be "1" when "$R_1$" is a single ring cyclic moiety comprising an "NO" group with one unpaired electron localized around the nitrogen atom, e.g. $R_1$ may be 2,2,6,6-tetramethyl-4-coboxyl piperidene-1-oxyl.

In the structure I or II above either the "$R_2$" or "$R_3$" may be bound not to the "O" but to an "NH" connecting moiety. When the "$R_2$" and "$R_1$" are each connected by an "NH" the resulting structure III as shown below is obtained.

FIG. 3

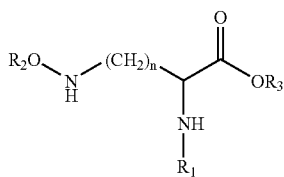

Compounds of the invention are covered by the structure III above when the variables $R_1$, $R_2$, $R_3$ and "n" are as defined above for I and II.

In each of the structures I, II and III the $R_1$ moiety is defined and may be a nitroxyl radical with one unpaired electron which nitroxyl radical may be a cyclic nitroxyl as shown in structure IV below.

Compounds of the invention are exampled by the general structural formula IV:

FIG. 4

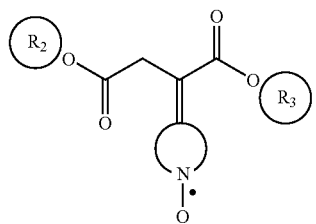

wherein $R_2$ and $R_3$ are each independently a moiety as defined above relative to any of the structures I, II, or III and in particular $R_2$ and $R_3$ may be methyl, ethyl, or butyl which may be tertiary butyl.

As used herein the circle can be any cyclic moiety with the —N— of the NO group at at least one position. The circle can be a six membered ring as in FIG. 5, a five membered ring as in FIG. 13 or other ring and/or fused ring structure.

Figure 7:
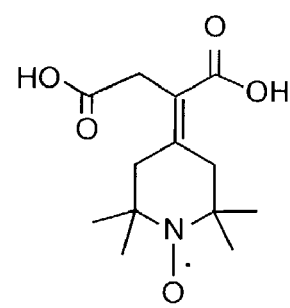
FIG. 7 shows the structure of FIG. 5 with $R_2$ and $R_3$ replaced by hydrogen referred as the compound 2,2,6,6-tetramethyl-1-oxyl-piperidinene-4-succinate (TOPS).
Figure 8:
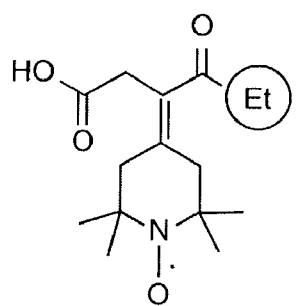
FIG. 8 shows the structure of FIG. 5 with R2 and R3 replaced by H and ethyl respectively referred as the compound of monoethyl-2,2,6,6-tetramethyl-1-oxy-4-piperidylidene-succinate (E-TOPS).
Figure 9:
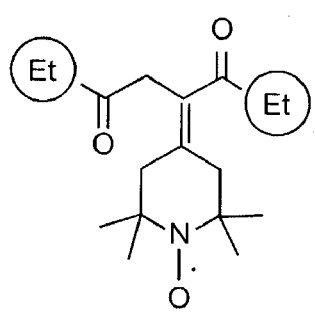
FIG. 9 shows the structure of FIG. 5 where the both $R_2$ and $R_3$ groups are an ethyl group, i.e. the Di-ethyl-2,2,6,6-tetramethyl-1-oxy-4-piperidylidene-succinate (DE-TOPS)
Figure 10:
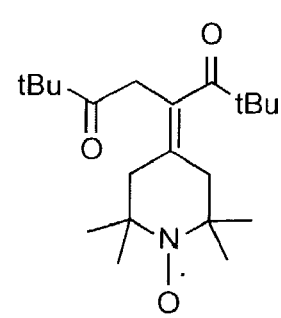
FIG. 10 shows the structure of FIG. 5 where the both R2 and R3 groups are tert butanol, i.e. the Di-tert-But 2,2,6,6-tetramethyl-1-oxy-4-piperidylidene succinate (DB-TOPS).
Figure 11:
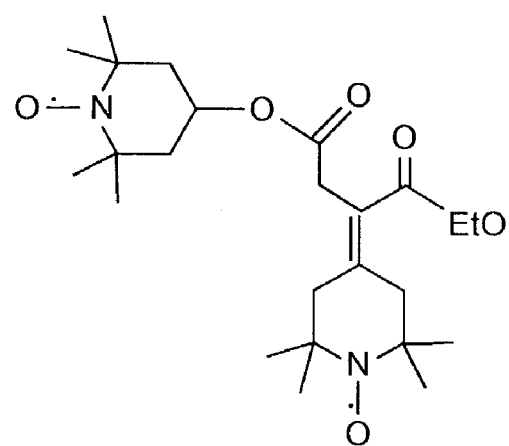
FIG. 11 shows the semi generic structure of FIG. 5 where $R_2$ is Tempol, i.e. TE-TOPS.
Figure 12:
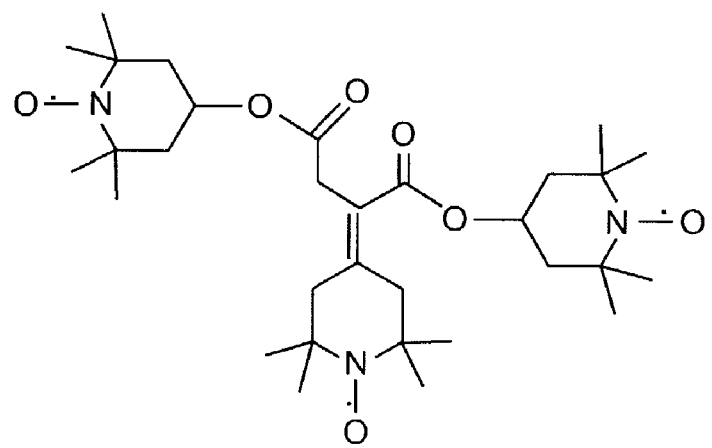
FIG. 12 shows the structure of FIG. 5 where $R_2$ and $R_3$ are both Tempol i.e. TT-TOPS.
Figure 13:
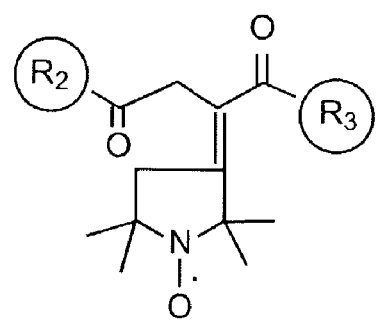
FIG. 13 shows the structure of FIG. 4 where the generic circle is a five membered ring.

In one structure where $R_2=R_3=$H (TOPS) in FIG. 7 is the structure within in viable cell after esterase cleavage which gives the efficacy of nitroxide intracellularly. In one embodiment the $R_2$ and (or) $R_3$ are themselves structures as per FIG. 11 and FIG. 12 FIG. 6 describes asymmetric structure with $R_2=$H and $R_3$ is each any moiety as defined above with respect to the structures of I, II and III. FIG. 8 gives an example of the FIG. 6 where $R_3=$ethanol (E-TOPS). FIG. 9 and FIG. 10 gives an example of symmetric structure of FIG. 5 where $R_2=R_3=$ethanol (DETOPS) or $R_2=R_3=$t butanol (DTTOPS). FIG. 11 gives an example of di-radical structure where $R_2=$Tempol (TETOPS).

In any structure of a compound of the invention the $R_2$ and $R_3$ may be used to bind the molecule to other atoms, molecules, or biological material. For example, in structure III the $R_2$ may be used to bind the molecules to other reactive cites as described in any of U.S. Pat. Nos. 5,725,839; 5,741,893; 5,767,089; 5,804,561; 5,807,831; 5,817,632; 5,824,781; 5,840,701; 5,591,710; 5,789,376; 5,811,005; 6,048,967. Further, the NH connected to the $OR_2$ group may be used to bind to other molecules such as a copper tri-peptide.

Since the compounds described herein provide a targeted therapeutic dose of antioxidant nitroxide, they are highly effective in preventing and alleviating the effects of oxidative stress. E-TOPS was found to have an increased in vivo half-life compared to Tempol via intravenous administration, intramuscular, oral, and intraperitoneal administration at 200 mg/kg. See FIGS. 18, 19, 20, and 21. The E-TOPS has also been demonstrated to have a very low acute toxicity profile compared to Tempol in an $LD_{50}$ model in mice (see FIG. 24).

Figure 35:
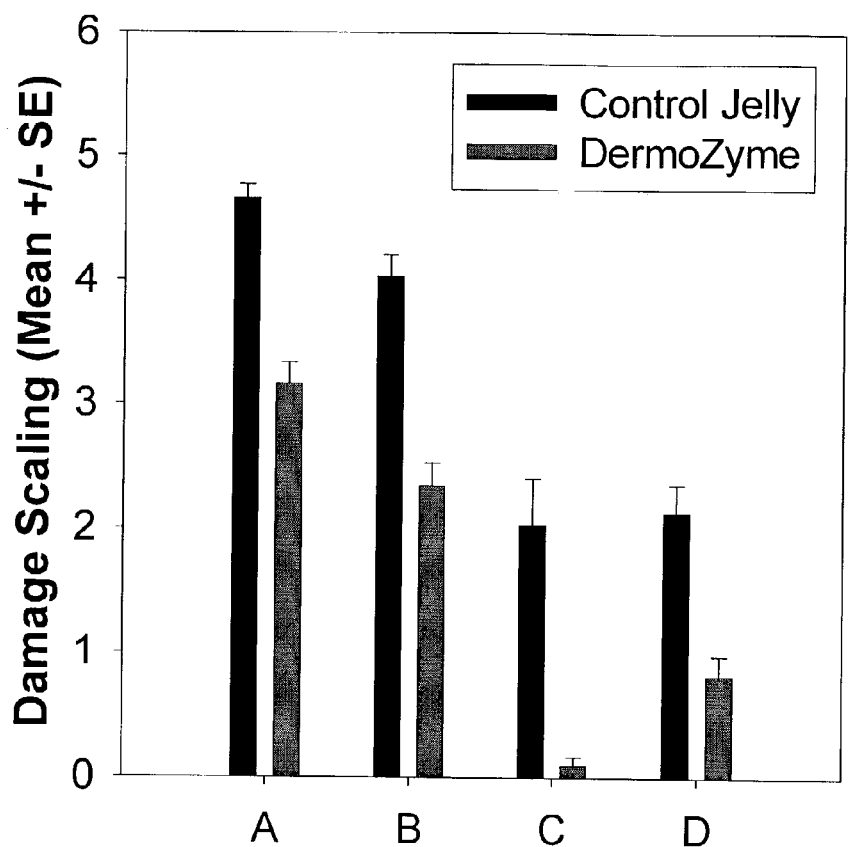
FIG. 35 shows the scores of the histopathological change of the hairless mouse skin after 11 days of UVB radiation with control or DE-TOPS applying post-radiation FIGS. 36(A, B and C) the comparison of effect of DE-TOPS with that of Tempol on UVB induced acute damage when applying 10 min or 2 hour pre radiation.
Figure 37:
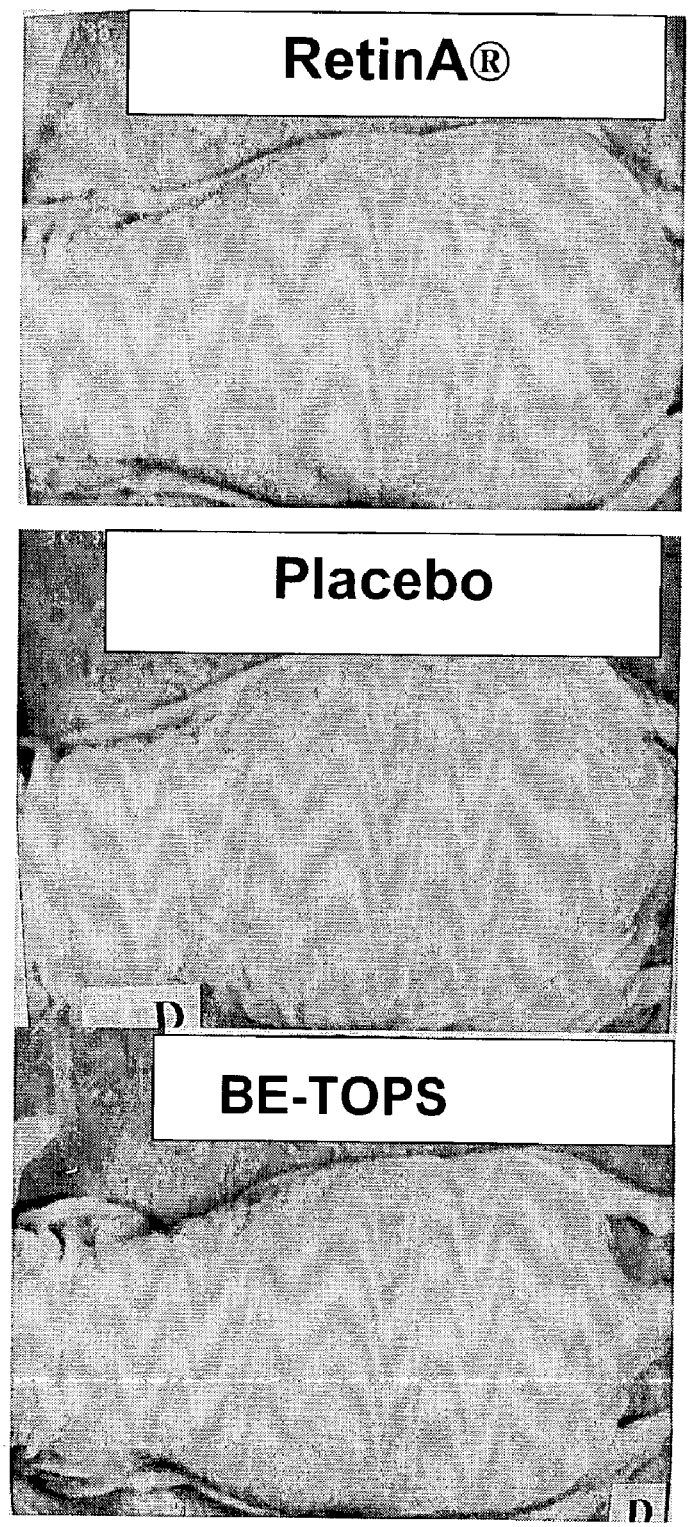
FIG. 37 (three panels) shows a comparison of DE-TOPS, a placebo, and Retin A 15 days after treatment with DE-TOPS and ultraviolet radiation.

In transdermal applications, the DE-TOPS (FIGS. 32, 35) formulation reduces UVB light induced skin thickening, hemorrhage, inflammation when applying pre and post radiation in mice. DE-TOPS also shows the effect on chronic lesion induced by UVB radiation (FIG. 33). These formulations also compare favorably to Retin A to reduce winkling (see FIG. 37). As described in more detail below, a major advantage of the CGN compounds of the present invention is the ability to administer a physiologically compatible solution in a variety of routes. Also, depending on the target cells and the diagnostic or therapeutic goal, the activity of these compounds may be enhanced by concurrent subcutaneous administration of a polynitroxide.

Compositions of the invention may be used in dermatologically/cosmetically acceptable vehicles for transdermal such as ointments, lotions, or gels, and other solvents or carriers acting as a dilutant, dispersant or carrier. The vehicle may comprise materials commonly employed in skin care products such as water, liquid or solid emollients, silicone oils, emulsifiers, solvents, humectants, thickeners, powders, propellants and the like.

As noted above, the unpaired nitroxyl electron gives nitroxides other useful properties in addition to the antioxidant activity. In particular, nitroxides in their free radical form are paramagnetic probes whose EPR signal can reflect metabolic information in biological systems, e.g., oxygen tension or tissue redox states. Because naturally occurring unpaired electrons are essentially absent in vivo, EPR imaging has the further advantage that there is essentially no background noise. Nitroxides also decrease the relaxation times of hydrogen nuclei, and are useful as contrast agents in proton or nuclear magnetic resonance imaging (MRI). Nitroxides can also act as contrast agents to add metabolic information to the morphological data already available from MRI. For example, by substituting various functional groups on the nitroxide, it is possible to manipulate properties including relaxivity, solubility, biodistribution, in vivo stability and tolerance. Contrast enhancement obtained from nitroxide can improve the performance of MRI by differentiating isointense, but histologically dissimilar, tissues and by facilitating localization and characterization of lesions, such as blood brain barrier damage, abscesses and tumors.

Formulations

In view of the stable chemical nature of the nitroxides, the compositions disclosed herein can be administered to a patient by various routes. For the purposes of this invention, "pharmaceutical" or "pharmaceutically acceptable" compositions are formulated by known techniques to be non-toxic and, when desired, used with carriers or additives that are approved for administration to humans. As described in the Examples below, the routes of administration include any type of injection including intramuscular, subcutaneous or intraperitoneal; intravenous, ocular or intraocular; oral; any type of transmucosal delivery including, bucal, nasal, anal, and vaginal; topical or transdermal; and intrapulmonary. Such compositions may include buffers, salts, or other solvents known to these skilled in the art to preserve the activity of the vaccine in solution.

A composition or formulation of the invention may comprise an effective amount of a nitroxide of the invention in a pharmaceutically acceptable excipient or carrier. The carrier is generally a relatively inert substance that facilitates administration of a pharmaceutically effective substance in a a dosage form suitable for delivery to a patient e.g. a human. Suitable excipients include by are not limited to stabilizing agents, wetting and emulsifying agents, salts for varying osmolarity, encapsulating agents, buffers, skin penetration enhancers, skin creams, and gels. Examples of pharmaceutically acceptable excipients are described in *Remington's Pharmaceutical Sciences* (Alfonso R. Gennaro, ed., 19$^{th}$ edition, 1995) incorporated here to disclose and describe carriers and formulations.

Topical formulations for application to the skin may comprise a nitroxide, a carrier, and sun block or UV absorber. A large number of UV absorbers are known as disclosed in any of U.S. Pat. Nos. 6,235,271; 6,224,854; 6,071,501; 5,976,513; 5,972,316; and 5,968,485 and patents and publications cited in these patents. The UV absorber may be any known oil-soluble organic UV absorber, especially those which are already approved and marketed for cosmetic use. Such oil-soluble organic UV absorbers are described, for instance, in "Sunscreens", Development, Evaluation and Regulatory Aspects, Eds.: N. J. Lowe and N. A. Shaath, M. Dekker Inc., New York and Basel, 1990; and Ken Klein, Encyclopedia of UV absorbers for sunscreen products, Cosmetics & Toiletries 107 45–64 (1992).

The oil-soluble, non-micronised UV absorber may be, for example, a p-aminobenzoic acid derivative such as an ester, salt or an amine-modified derivative of p-aminobenzoic acid; a salicylic acid derivative such as an ester or salt thereof; a benzophenone derivative; a dibenzoylmethane derivative; a diphenylacrylate derivative; a benzofuran derivative; a polymeric UV absorber containing one or more silico-organic residues; a camphor derivative; a trianilino-s-triazine derivative; phenylbenzimidazole sulfonic acid and its salts; urocanic acid (3-imidazol-4-yl-acrylic acid) or its ethyl ester; menthyl anthranilate; a benzotriazole; a hydroxyphenyltriazine derivative; or a bis-resorcinol-dialkylaminotriazine.

Specific examples of benzophenone derivatives include benzophenone-3-(2hydroxy-4-methoxybenzophenone), benzophenone-4 (2-hydroxy-4-methoxybenzophenone-5-sulfonic acid) and benzophenone-8-(2,2'-dihydroxy-4-methoxybenzophenone).

A specific example of a dibenzoylmethane derivative is butyl methoxydibenzoylmethane [1-(4-tert.-butyl)-3-(4-methoxyphenyl)propane-1,3-dione].

Specific examples of a diphenylacrylate derivative include octocrylene (2-ethylhexyl-2-cyano-3,3'-diphenyl acrylate) and etocrylene (ethyl-2-cyano-3,3'-diphenyl acrylate).

Specific examples of a benzofuran derivative include the 3-(benzofuranyl)-2-cyanoacrylates described in U.S. Pat. No. 5,338,539 or EP 582189, the 2-(2-benzofuranyl)-5-tert.-butylbenzoxazoles described in U.S. Pat. No. 5,518,713 and the 2-(p-aminophenyl)benzofurans described in U.S. Pat. No. 5,362,481.

Specific examples of a polymeric UV absorber containing one or more silico-organic residues are the benzylidenemalonate silicone derivatives disclosed in EP 709080 in which R.sub.15 is H or OMe and r is approximately 7; and the polymers of the benzotriazole silicone type described in WO 94/06404.

Specific examples of a cinnamate ester include octyl methoxy cinnamate (4-methoxycinnamic acid 2-ethylhexyl ester), diethanolamine methoxy cinnamate (diethanolamine salt of 4-methoxycinnamic acid), isoamyl p-methoxycinnamate (4-methoxycinnamic acid 2-isoamyl ester), 2,5-di-isopropyl methyl cinnamate, the cinnamido derivatives disclosed in U.S. Pat. No. 5,601,811 and the derivatives described in WO 97/00851.

Specific examples of camphor derivatives are 4-methyl-benzylidene camphor [3-(4'-methyl)benzylidene-bornan-2-one], 3-benzylidene camphor (3-benzylidene-bornan-2-one), polyacrylamidomethyl benzylidene camphor {N-[2 (and 4)-2-oxyborn-3-yliden-methyl)benzyl]acrylamide polymer}, trimonium benzylidene camphor sulfate [3-(4'-trimethylammonium)-benzylidene-bornan-2-one methyl sulfate], terephthalydene dicamphor sulfonic acid {3,3'-(1, 4-phenylenedimethine)-bis-(7,7-dimethyl-2-oxo-bicyclo-[2.2.1]heptan-1-methanesulfonic acid} and salts thereof and benzylidene camphor sulfonic acid [3-(4'-sulfo)benzylidene-bornan-2-one] and salts thereof.

Specific examples of trianilino-s-triazine derivatives include octyl triazine [2,4,6-trianilino-(p-carbo-2'-ethyl-1'-oxy)-1,3,5-triazine, the trianilino-s-triazine derivatives disclosed in U.S. Pat. No. 5,332,568, the trianilino-s-triazine derivatives described in EP 517104, trianilino-s-triazine derivatives disclosed in EP 570838, the trianilino-s-triazine derivatives described in U.S. Pat. No. 5,252,323, the trianilino-s-triazine derivatives described in WO 93/17002-A1 and the trianilino-s-triazine derivatives disclosed in WO 97/03642-A1.

A specific example of a benzotriazole is 2-(2-hydroxy-5-methyl-phenyl)benzotriazole.

Specific examples of hydroxyphenyltriazine derivatives include, e.g. those described EP-A1-775,698, such as 2,4-bis-{[4--(2-ethyl-hexyloxy)-2-hydroxy]-phenyl}-6-(4-methoxyphenyl)-1,3,5-triazine.

Specific examples of bis-resorcinol-dialkylaminotriazines are, e.g., those described in EP-A1-780,382.

The inorganic micropigment UV absorber, the optional component b) of the new sun protection agent may be, for example, titanium dioxide coated with aluminium oxide or silicon dioxide, zinc oxide coated with aluminium oxide or silicon dioxide, or mica.

The polymeric hollow sphere component, component c) of the new sun protection agent according to the present invention, may be, for instance, those described in EP-A-761,201.

Methods

A method of treatment is disclosed whereby a nitroxide compound is administered to a patient in a therapeutically effective amount. The nitroxide compound is comprised of a first portion which comprises a nitrogen atom and an oxygen atom bound directly together and an unpaired electron (•NO), and a second portion which provides a negative charge. The first and second portions are connected directly or indirectly by a linking group positioned between and bound to the first portion and the second portion in a manner such that the negative charge of the second portion stabilizes the •NO of the first portion when the nitroxide is present in the patient. By stabilizing the •NO portion of the molecule the nitroxide is allowed to interact with reactive oxygen species in the patient for a longer period of time and modulate adverse effects of those reactive oxygen species.

A method is disclosed whereby a formulation is applied to the skin of a patient which may be a human. The formulation is comprised of a carrier and a compound which has a first lipid solubility and a first aqueous solubility. The compound is allowed to permeate the patient's skin and reach viable cells and react in the presence of enzymes of the cells. The reaction results in a compound which has a second lipid solubility which is substantially less than the first lipid solubility and also obtain a second aqueous solubility which is substantially greater than the first aqueous solubility thereby allowing the compound to permeate to viable cells and remain in contact with those cells. The compound may be a nitroxide which aids in modulating adverse effects of reactive oxygen species.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Synthesis and Preparation of Mono and Dicarboxylic Acid and Esterified Nitroxide Species The following chemical synthesis protocols yield stable nitroxide free radicals whose physiological compartmentalization, as a function of membrane permeability and clearance in vivo, is regulated by a negatively charged anion such as mono- or di-carboxylic acids. Topical applications are particularly advantageous with ester derivatives that provide differential permeability across hydrophobic barriers with a first nitroxide species having increased membrane permeability relative to a second species having increased intracellular retention and antioxidant therapeutic utility after hydrolysis by intracellular esterases.

(a) Synthesis of Monoethyl and Diethyl2,2,6,6,-Teteramethyl-1-oxyl-4-piperidinyl succinate (E-TOPS) and (DE-TOPS).

A dry, two-necked flask fitted with a reflux condenser and magnetic stirrer is charged with 45 ml of absolute tert-butanol and 6.72 g of potassium tert-butoxide under nitrogen atmosphere. The mixture is boiled and heated under reflux until all solids are dissolved. The flask is then cooled and 6.8 grams of 4-oxo-[TPO], 12 ml of diethyl succinate and 15 ml of tertiary butanol is added. The reaction mixture is then heated for 10 minutes. After cooling with ice, and neutralizing with dilute HCL, the bulk of the alcohol is distilled off under reduced pressure. The residue is poured into 350 ml of ice water and acidified with dilute hydrochloric acid to pH 3, and extracted with methylene chloride. The combined extracts are washed several times with a 1% ammonia solution. The solutions are cooled with ice, acidified and extracted again with methyl chloride. The resulting extract is then dried with sodium sulfate. After evaporation of the methylene chloride, the remaining oily red liquid is triturated with hexane. The crystal of the monoester is pressed on a porous porcelain plate and recrystallized from a mixture of ether and hexane. The product is a yellow prism with a melting point of 103° C., and the expected yield is in the 60–70% range.

Figure 14:
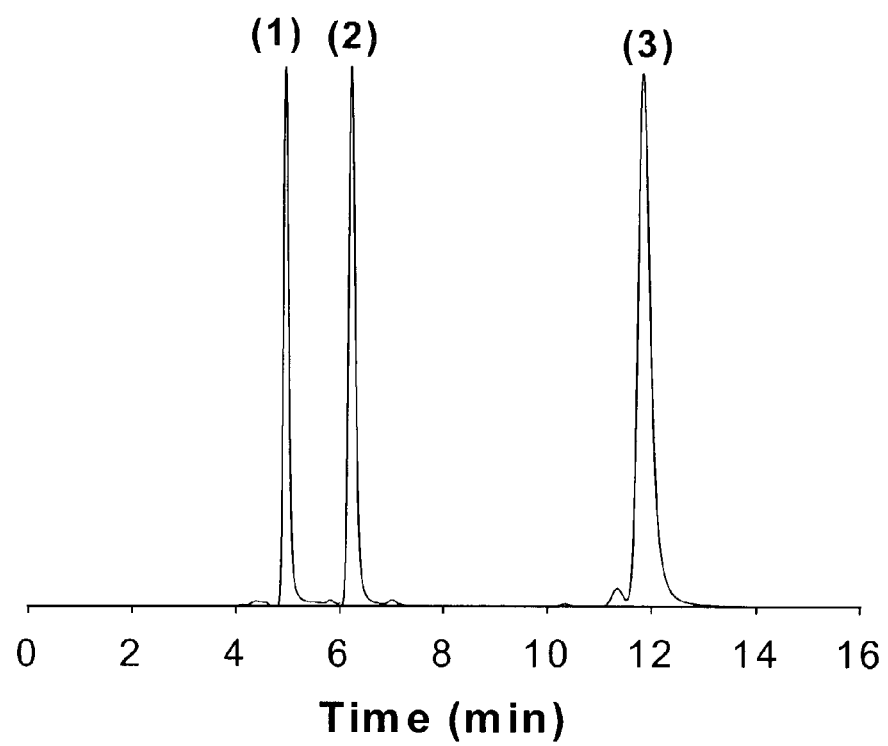
FIG. 14 shows a liquid chromatograph spectrum identifying TOPS and its ester(s) of carboxylic acid derivatives, E-TOPS and DE-TOPS.

FIG. 14 shows the separation of TOPS, E-TOPS, and DE-TOPS by liquid chromatography.

Example 2

Hydrolysis of DE-TOPS to TOPS

Figure 15:
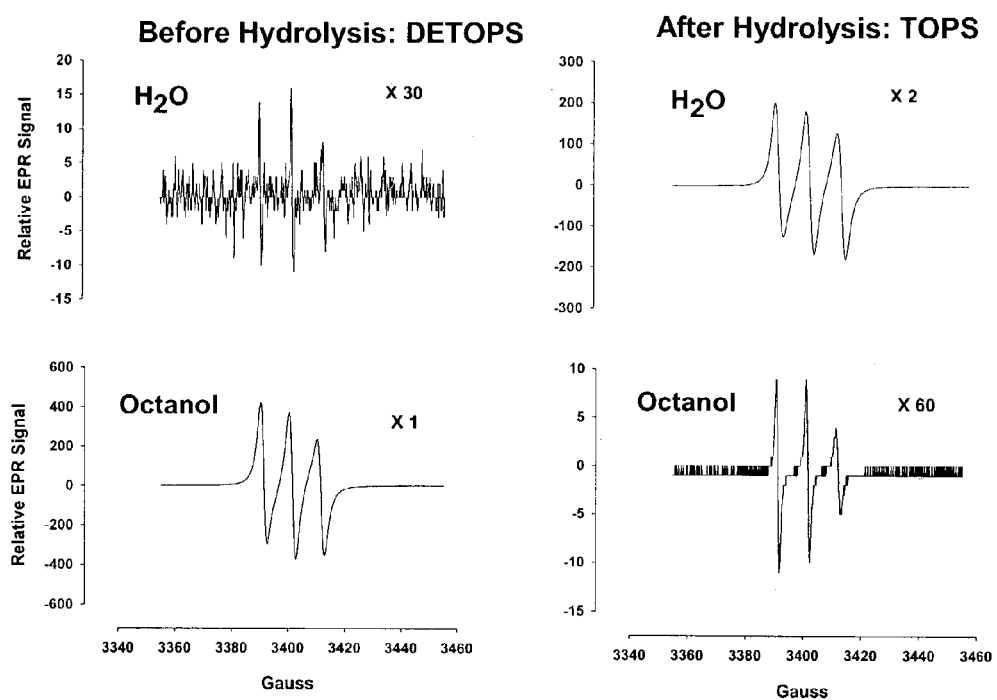
FIG. 15 shows the hydrolysis of DE-TOPS to TOPS by sodium hydroxide (NaOH) in an aqueous environment. As is apparent from the EPR signals, pre- and post-hydrolysis, near complete conversion from DE-TOPS to TOPS occurs.

Referring to FIG. 15, the hydrolysis of DE-TOPS to the non-esterified TOPS form will yield selective cell membrane permeability and increased intracellular retention when the nitroxide compounds are exposed to esterases or any intracellular enzyme or other biochemical reaction that cleaves the ester group. The application of DE-TOPS as a hydrophobic pro-drug will penetrate the stratum corneum (dead cells) into the metabolically active base-membrane layers. Enzymatic hydrolysis of DE-TOPS will allow the product TOPS to be retained in the aqueous phase and hopefully and primarily in the intracellular volume. To demonstrate this reaction, chemical hydrolysis of DE-TOPS is shown to yield a compound which preferentially distributes in water vs. octanol.

A 20 mg sample of DE-TOPS was added to a mixture of 1 ml water and 1 ml octanol and allowed to partition. After 15 minutes, a 40 µl sample of water or oil was taken for EPR spectral analysis. Next, 20 mg of DE-TOPS was mixed in 1 ml of 10 mM NaOH and allowed to incubate overnight at room temperature. The solution was neutralized with hydrochloric acid and added to 1 ml of water and 2 ml of octanol. The mixture was allowed to partition, and after 15 minutes, a 40 µl sample of water or oil was taken for EPR spectral analysis. EPR spectral were taken using a Varian E9 spectrophotometer. Sweep width was 100 G, frequency was 9.535 GHz, microwave power was 2 mV and the modulation frequency was 100 Hz.

Before hydrolysis, DE-TOPS was preferentially distributed in octanol. The partition coefficient (LogP) for DE-TOPS was found to be 1.7. After hydrolysis, the presumed product TOPS partitions in the aqueous phase. The partition coefficient (LogP) for TOPS was found to be −0.9. This shows that following hydrolysis, the product thus formed is significantly hydrophilic and would be more readily compartmentalized intracellularly.

Example 3

Synthesis of TE-TOPS

Figure 16:
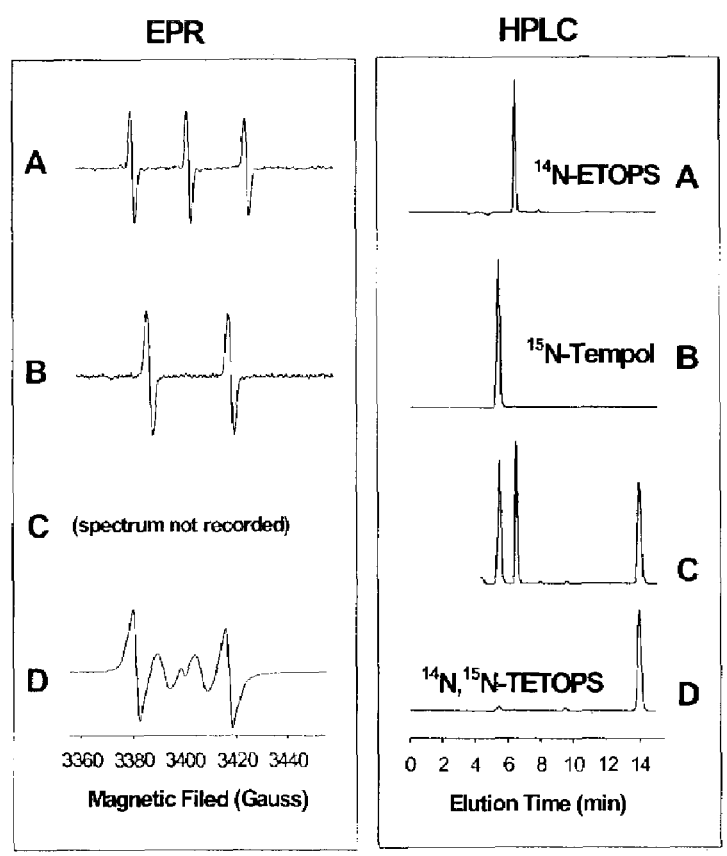
FIG. 16 shows liquid chromatograph HPLC and EPR spectra describing the structure changes during the synthesis of TE-TOPS from $^{14}N$ E-TOPS and $^{15}N$ Tempol.

This pilot study is to synthesize TE-TOPS as the proof of Tempol, excising compound may be incorporated into the TOPS-ester prodrug construct. TE-TOPS was synthesized from the $^{14}$N-E-TOPS and $^{15}$N-Tempol. The synthesis is a multi-step process involving condensation of oxo-Tempo (4-oxo-2,2,6,6-tetramethyl-piperidine-1-oxyl) with diethyl-succinate followed by esterification of the $^{14}$N-E-TOPS with either $^{15}$N-Tempol or ethanol, yielding $^{14}$N-DE-TOPS or $^{14}$N-,$^{15}$N-TE-TOPS, respectively. The reaction to form the bi-radical $^{14}$N, $^{15}$N-TE-TOPS was monitored by both HPLC and EPR. $^{14}$N-E-TOPS gives a triplet EPR spectrum as shown in FIG. 16A left panel. Its HPLC elution time is 6.3 min as shown in FIG. 16, right panel. $^{15}$N-Tempol gives a doublet EPR spectrum as shown in FIG. 16B, left panel. The HPLC elution time for $^{15}$N-Tempol is 5.3 min as shown in FIG. 16B, right panel. After 3 hours reaction, the height of the HPLC peaks at 5.3 and 6.3 min decreased while a new peak at 13.9 min appeared (see FIG. 16C, right panel). After 6 hours of reaction, $^{15}$N-Tempol and $^{14}$N-E-TOPS peaks almost disappeared (FIG. 16D, right panel). To ensure the HPLC peak at 13.9 min consists of $^{14}$N-, $^{15}$N-TE-TOPS, the peak was collected then assayed by EPR. The EPR spectrum is shown in FIG. 16D, left panel. The broadening and appearance of new peaks are due to spin-spin and spin-spin dipole interactions between the bi-radicals.

Example 4

Hydrolysis of TE-TOPS to TOPS and Tempol 20 mg of $^{14}$N-$^{15}$N-TE-TOPS was mixed in 1 ml of 10 mM KOH and allowed to incubate overnight at room temperature. The solution was neutralized with hydrochloric acid. EPR spectral were taken using a Varian E9 spectrophotometer. Sweep width was 100 G, frequency was 9.535 GHz, microwave power was 2 mV and the modulation frequency was 100 Hz. A sharper EPR spectrum in FIG. 17A indicated that TE-TOPS was fully hydrolyzed in comparison with the broad spectrum in FIG. 16D left panel. $^{15}$N-$^{14}$N-TE-TOPS in topical cream were applied on mouse skin. The urine sample showed the esterase cleavage in vivo see FIG. 17B

Example 5

In Vivo Plasma Half-Life of DE-TOPS and Tempol

Figure 24:
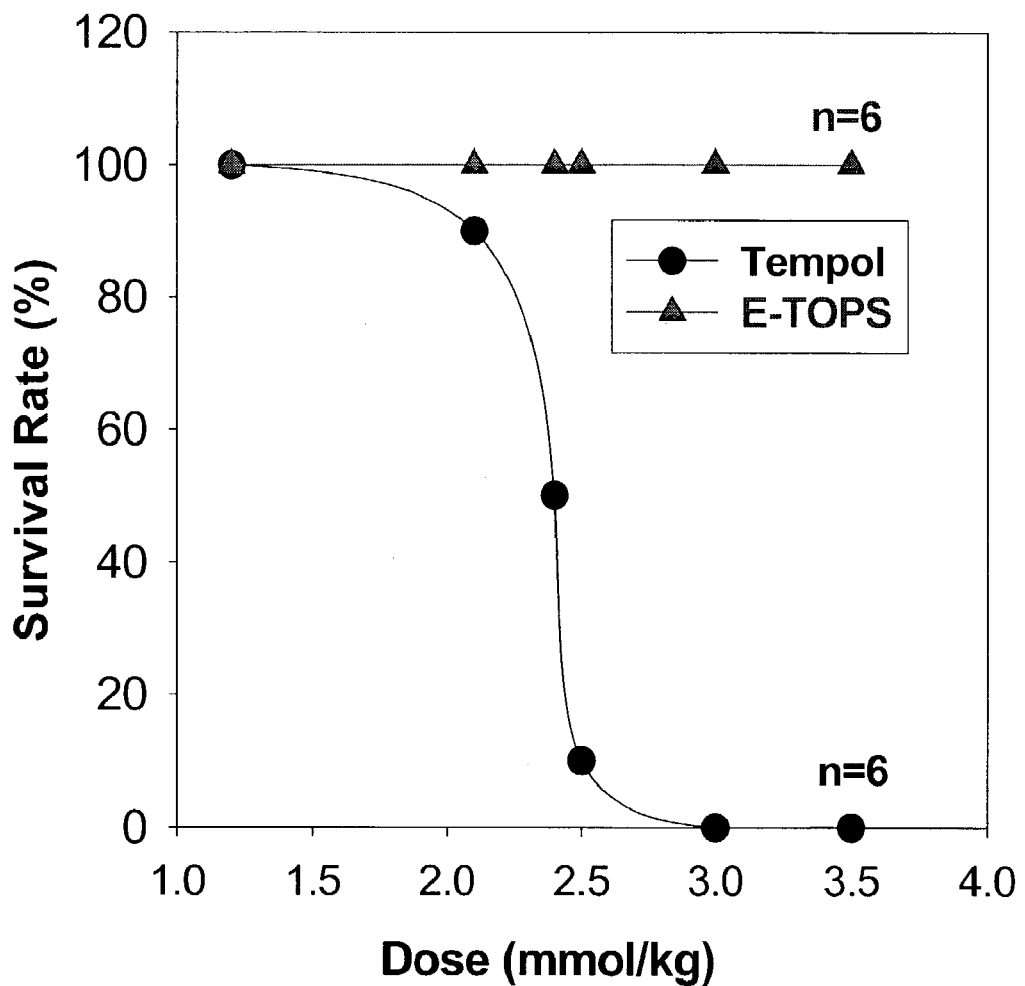
FIG. 24 shows the relationship between the survival rate and dosage for E-TOPS compared to Tempol in an $LD_{50}$ study in mice.

As noted above, a principal drawback in existing nitroxide-based compositions for in vivo therapeutic or diagnostic use is the limited half-life of these molecules and their rapid in vivo bioreduction and clearance. The result of the comparatively short half life of Tempol is a need to administer larger and larger doses to yield a profound therapeutic or diagnostic effect. As shown in FIG. 24 below, the increased dosages of nitroxides can yield acute and chronic toxicity. However, where the plasma half-life of a compound is increased, the overall dosage in both acute and chronic indications can be reduced.

Figure 18:
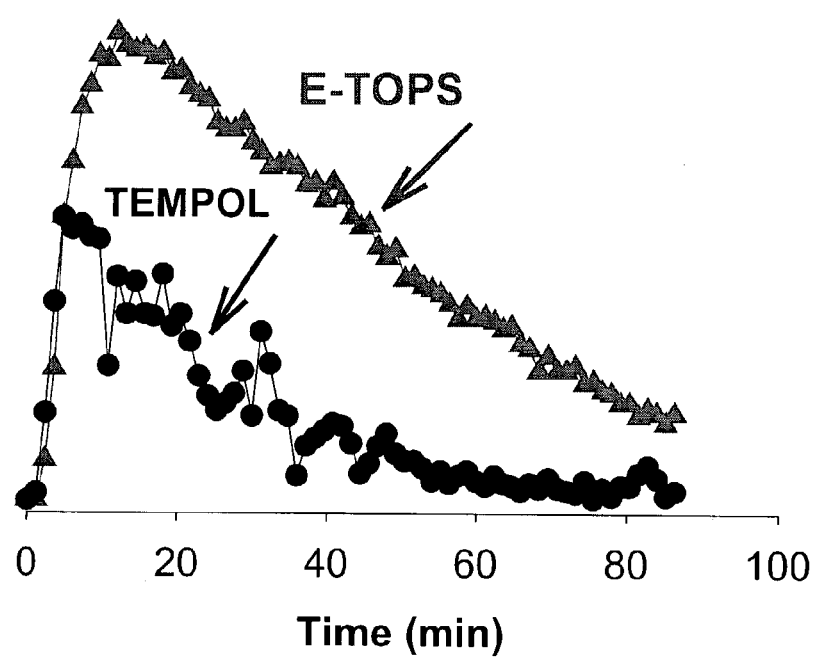
FIG. 18 shows the extended in vivo plasma half-life of $^{14}N$ E-TOPS compared to $^{15}N$ Tempol when both are co-administrated intraperitoneally in mice.

Plasma half-life is measured by collecting the spectrum each minute for 60 to 90 minutes. The peak height of $^{15}$N Tempol or $^{14}$N E-TOPS EPR signal is calculated from each spectrum. The peak height of TempolL or E-TOPS is plotted against time as shown in FIGS. 18–21 for i.p., i.v., i.m., and oral respectively. FIG. 18 shows a measurement of the in vivo plasma half-life of an i.p.administration of E-TOPS and Tempol at 125 mg/kg. $^{14}$N E-TOPS (upper line) is substantially enhanced for the entire half-life of the compounds. Although $^{15}$N Tempol (lower line) has a measurable half-life exceeding 40 minutes, E-TOPS has substantially higher activity for at least 80 minutes. The doses are 125 mg/kg of E-TOPS and 80 mg/kg Tempol at a 1:1 molar ratio.

Figure 19:
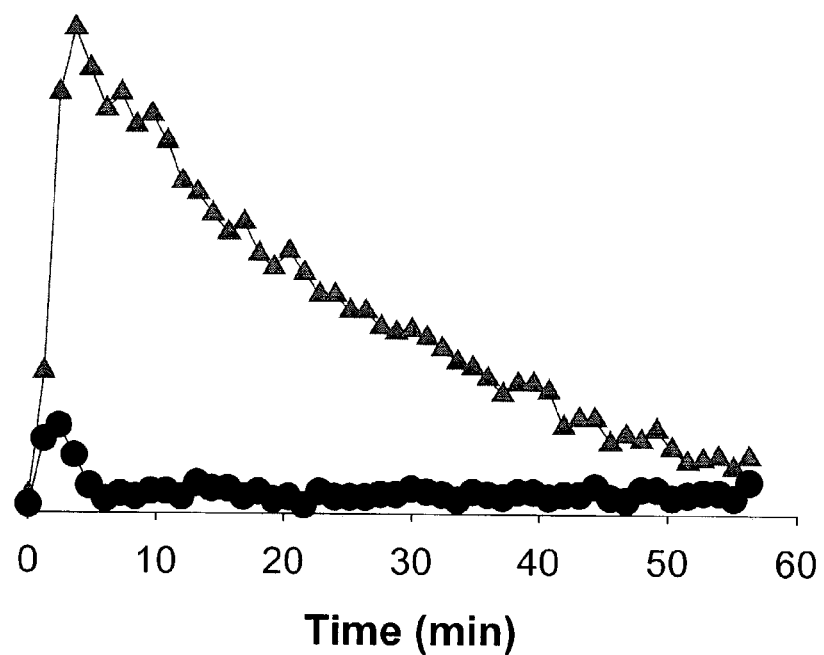
FIG. 19 shows the extended in vivo plasma half-life of $^{14}N$ E-TOPS compared to $^{15}N$-Tempol when both are co-administrated intravenously in mice.

FIG. 19 shows a measurement of the in vivo plasma half-life of an intravenous administration of E-TOPS and Tempol at 125 mg/kg. In the intravenous infusion example, Tempol (lower line) is rapidly reduced in vivo such that, by the five-minute mark after infusion, very little active Tempol remains in the intravascular space.

Figure 20:
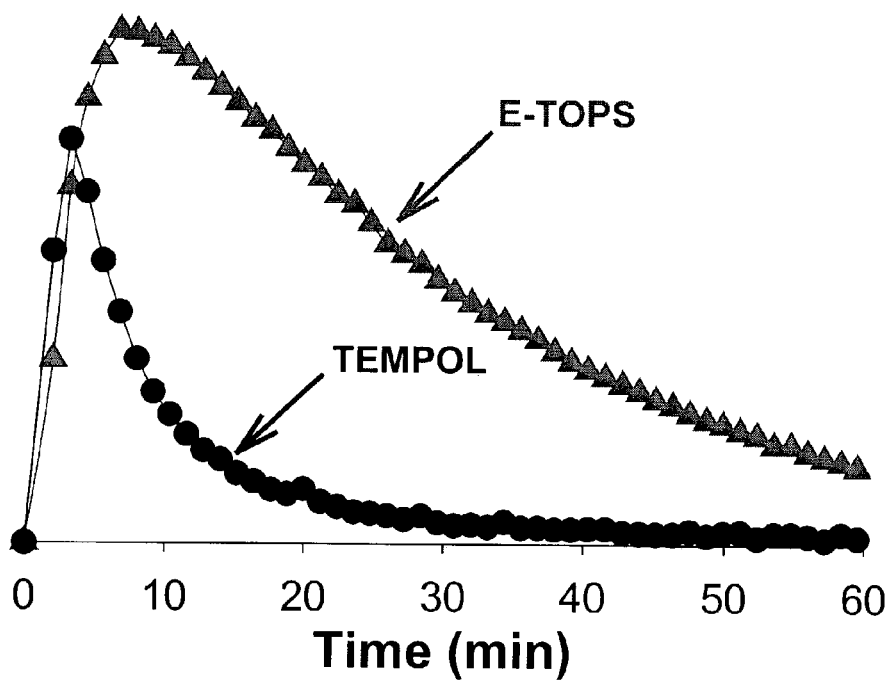
FIG. 20 shows the extended in vivo plasma half-life of $^{14}N$-E-TOPS compared to $^{15}N$-TEMPOL when both are co-administrated intramuscularly in mice.

As is shown in FIG. 20, beyond the first few minutes the in vivo plasma half-life of E-TOPS is dramatically extended over Tempol for at least 60 minutes following intramuscular co-administration.

Figure 21:
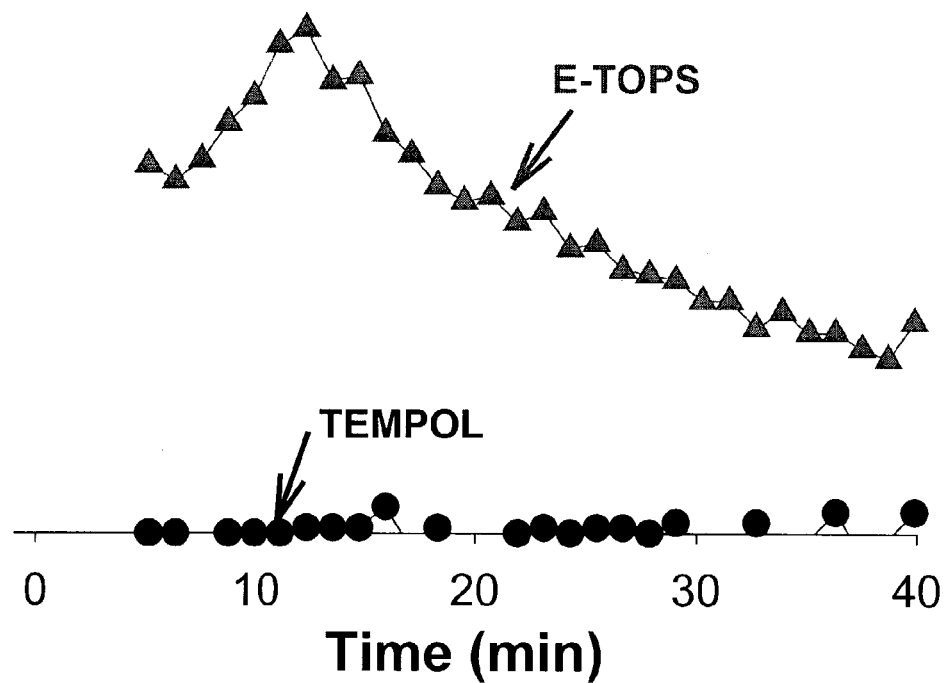
FIG. 21 shows the extended in vivo plasma half-life of $^{14}N$-E-TOPS compared to $^{15}N$-Tempol L when both are co-administrated orally in mice.

Referring to FIG. 21, the in vivo plasma half-life of E-TOPS compared to Tempol is shown to be extended when both compounds are administered orally. As in FIGS. 18–21, the doses are 125 mg/kg of E-TOPS and 80 mg/kg of Tempol at 1:1 molar ratio Example 6

Penetration and Compartmentalization in Human Skin

Figure 22:
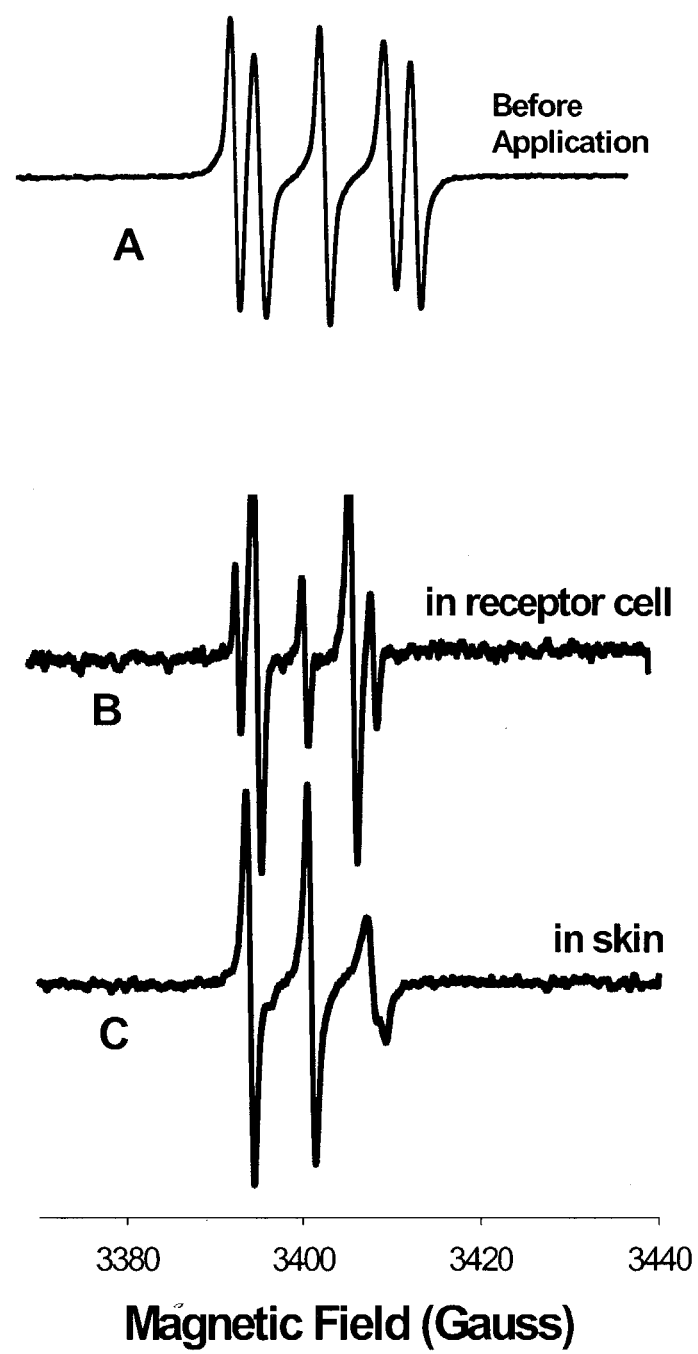
FIGS. 22A–C shows skin penetration and compartmentalization of DE-TOPS in a Franz Diffusion cell when $^{14}N$-DE-TOPS and $^{15}N$-Tempol are co-applied on hairless mouse skin: 22A—before application; 22B—in receptor cell; and 22C in skin at 20 hours.

Referring to FIG. 22, DE-TOPS (100 mM) in a petroleum base was applied on fresh human skin. The receptor buffer is PBS with 0.01% sodium azide. The buffer was constantly stirring. The cell was maintained at 37 C. with a circulating water bath. FIG. 22 shows the degree of skin penetration. Mouse skin (or donor human skin) to cover the top of the receptor and cell DE-TOPS is applied on top of the skin. Under the skin, PBS buffer is applied to keep the skin alive. 24 hours later the buffer will be collected for EPR assay. The surface of the skin is cleaned and the skin sample tested for EPR Signal. Although Tempol and DE-TOPS have same signal intensity prior to application, twenty-four hours after application a stronger Tempol signal exists in the buffer compound to DE-TOPS. However, in the skin the E-TOPS signal is stronger than Tempol. Thus, DE-TOPS is localized in skin compared with Tempol. DE-TOPS will penetrate into the cells of the epidermis and dermis where it will be enzymatically hydrolyzed and become compartmentalized. Compared to the freely soluble Tempone, this would result in a more uniform distribution of DETOPS in these skin layers.

Preliminary S-band EPR spectroscopy and imaging experiments using DETOPS were performed on the skin of a human volunteer. The human volunteer's forearm skin, about 6 mm diameter circular spot, typically at the lunar surface of the wrist, was washed thoroughly with alcohol and 3 μL of 100 mM DE-TOPS solution (about 2×10$^{17}$ spins) was applied to the marked skin area. Five minutes later, when the deposited solution dried, a specially designed positioning holder with a 7 mm diameter well and bottom disk that locked into a well in the resonator cap was attached to the skin to fix this region of skin to the surface resonator See, "In vivo EPR Imaging of a Distribution and Metabolism of Nitroxide Radicals in Human Skin," He et al., J. of Magnetic Resonance 148, 155–164 (2001). EPR and EPRI measurements were then started. Measurements on the volunteer were performed for 15 to 20 minutes periods after which there were 30-minute rest periods in which the volunteer removed the arm from the resonator and the magnet. This holder fixed the skin positioning and assured a constant filling factor of the loaded resonator. The positioning holder was left attached to the arm for the entire series of measurements lasting up to 8 hours.

Figure 23:
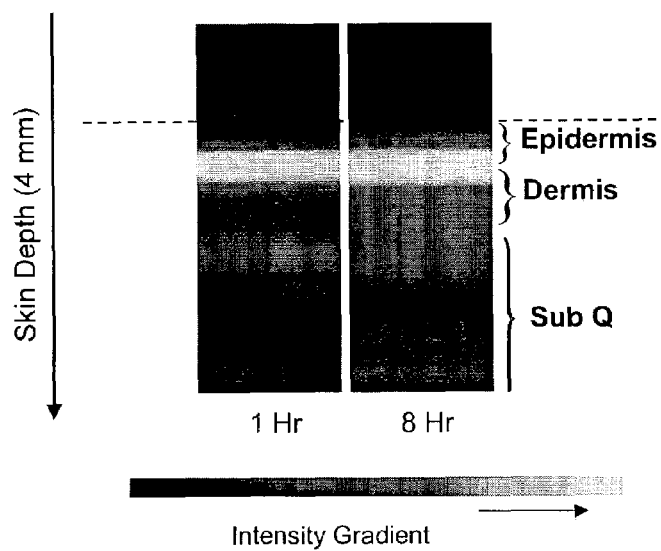
FIG. 23 shows human skin penetration and compartmentalization of DE-TOPS by EPRI.

Referring to FIG. 23, a color-coded image of CNO penetration and compartmentalization in human skin is shown. The 1-D spatial images were obtained from the skin of the fore-arms of the same human volunteer at 1 hr and 8 hr post-topical application of 3 μL or DE-TOPS (100 mM in DMSO). The measurements were performed using S-band (2.2 GHz) EPR imaging system with a specially designed surface resonator as described in He et al., J. of Magnetic Resonance 148, 155–164 (2001). The dotted line marks the surface of the skin. The estimated skin depths are marked as epidermis, dermis and subcutaneous layers. Compartmentalization results in a more diffuse distribution of DE-TOPS throughout the skin layers. The 1-D EPR spatial image of DE-TOPS compared to tempone show an enhanced visual distribution throughout the dermis and epidermis by eight hours.

Example 7

Acute Toxicity $LD_{50}$ of Tempol and E-TOPS as Well as Metabolisms of E-TOPS

Figure 25:
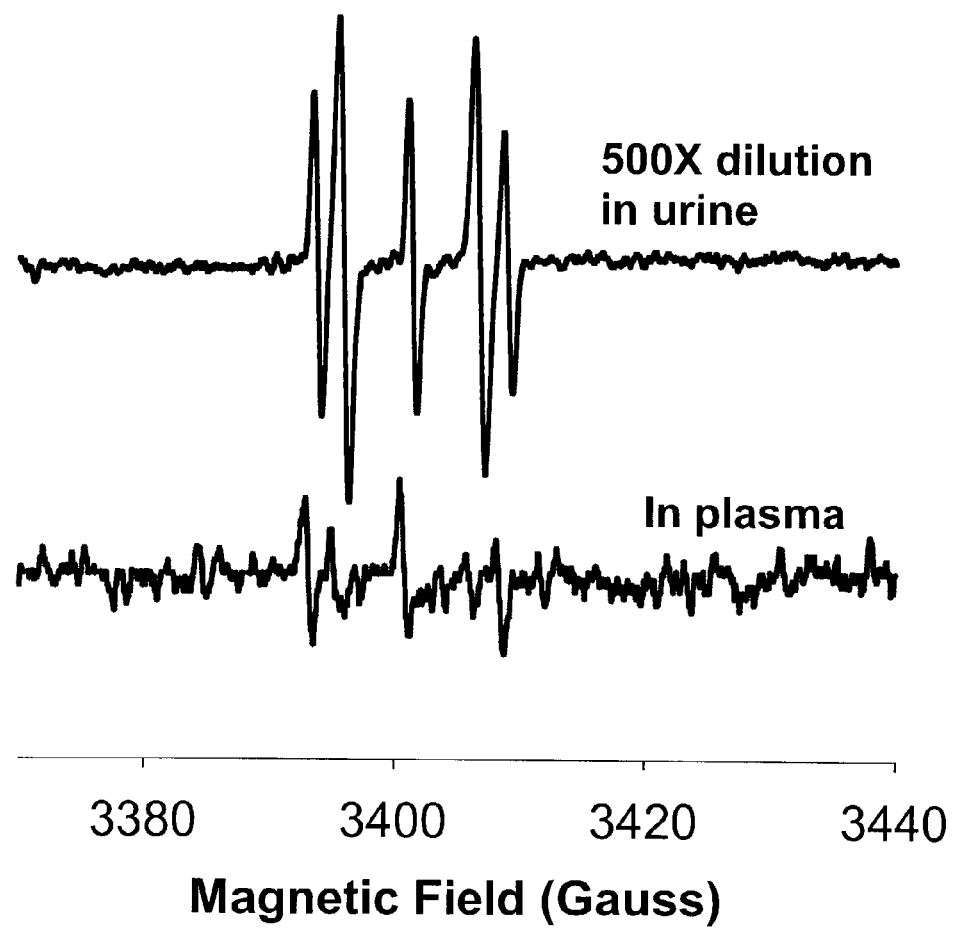
FIG. 25 shows the metabolism of DE-TOPS through excretion in urine and reduction in plasma after 10 day daily topical application.

As noted above, the practical, clinical application of unbound, small molecule nitroxides has been limited by the reduced activity in vivo and comparatively short in vivo half-life. The result of the reduced in vivo half-life is the need to administer a larger dose to achieve the same therapeutic or diagnostic effect. The toxicity of Tempol may be measured with an $LD_{50}$ model to determine the survival rate of mice at varying dosages. FIG. 24 shows the acute toxicity curve for Tempol as a function of survival rate with increasing dosages. The E-TOPS formulation shows essentially no decrease in survival rate at dosages up to 3.5 mmol/kg whereas Tempol shows zero survival rate at the lower dosage of 2.0 mmol/kg. Significant differences in survival rate appear between the dosage of 2.0–2.5 mmol/kg. FIG. 25 shows the stronger EPR signal (proportional to concentration) from DE-TOPS in urine compound for plasma after 6 hours, showing excretion and clearance through normal metabolism.

Example 8

Inhibition of Superoxide Dismutases Activity of E-TOPS

Figure 26:
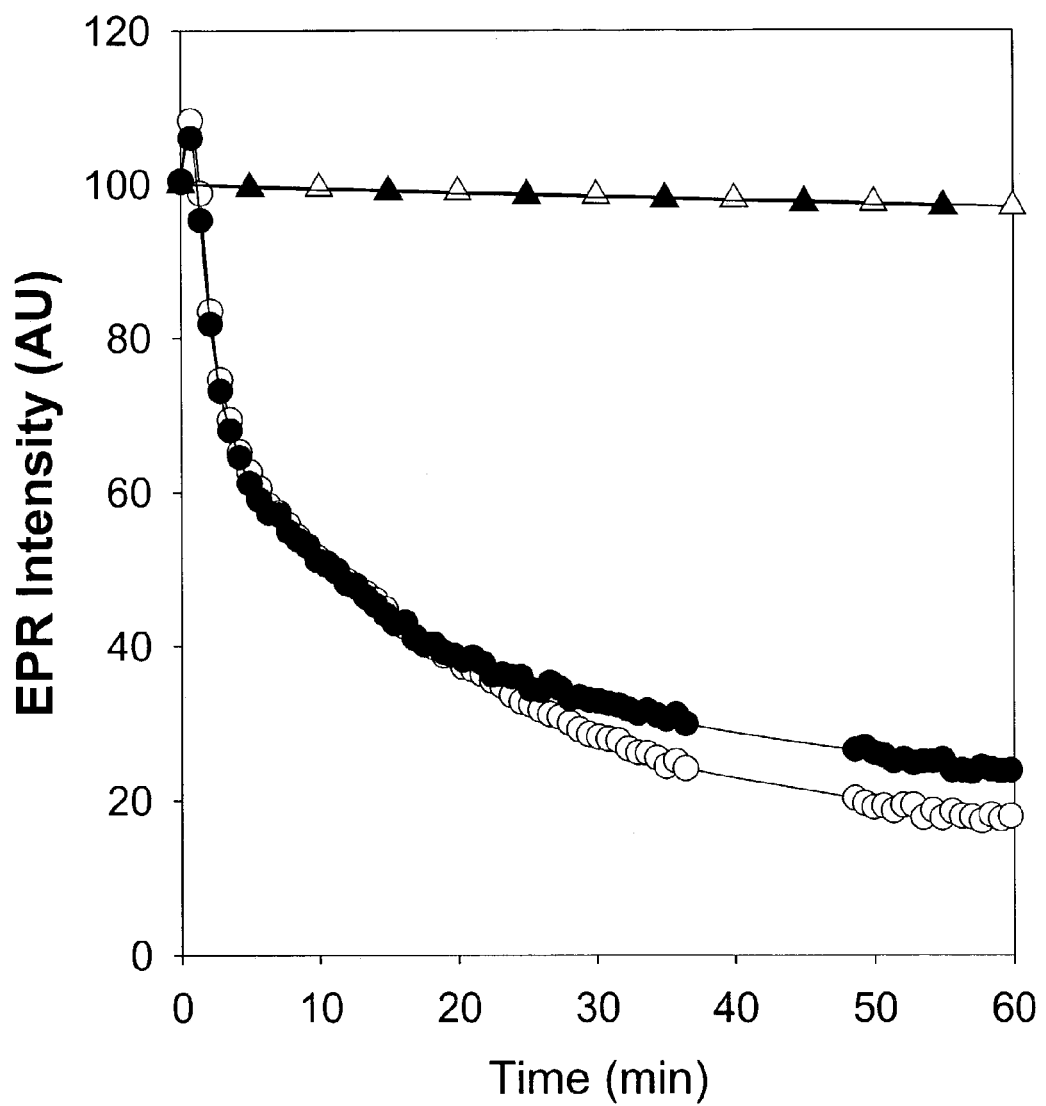
FIG. 26 shows the superoxide dismultase activity of E-TOPS determined by EPR.

Superoxide dismutase activity of E-TOPS in comparison with Tempol are shown in FIG. 26. SOD-mimetic activity of E-TOPS and Tempol was measured by electron paramagnetic resonance. High-filed EPR peak was monitored with time. E-TOPS and Tempol without NADH (−NADH) curve showed nitroxide reacts with superoxide catalytically. E-TOPS and Tempol with NADH (+NADH) curves showed two-electron reduction from oxoammonium to hydroxylamine. The result showed that E-TOPS had the similar SOD activity as Tempol.

Example 9

Hemoglobin Toxicity in Cultured Rat Cortical Neurons

Figure 27:
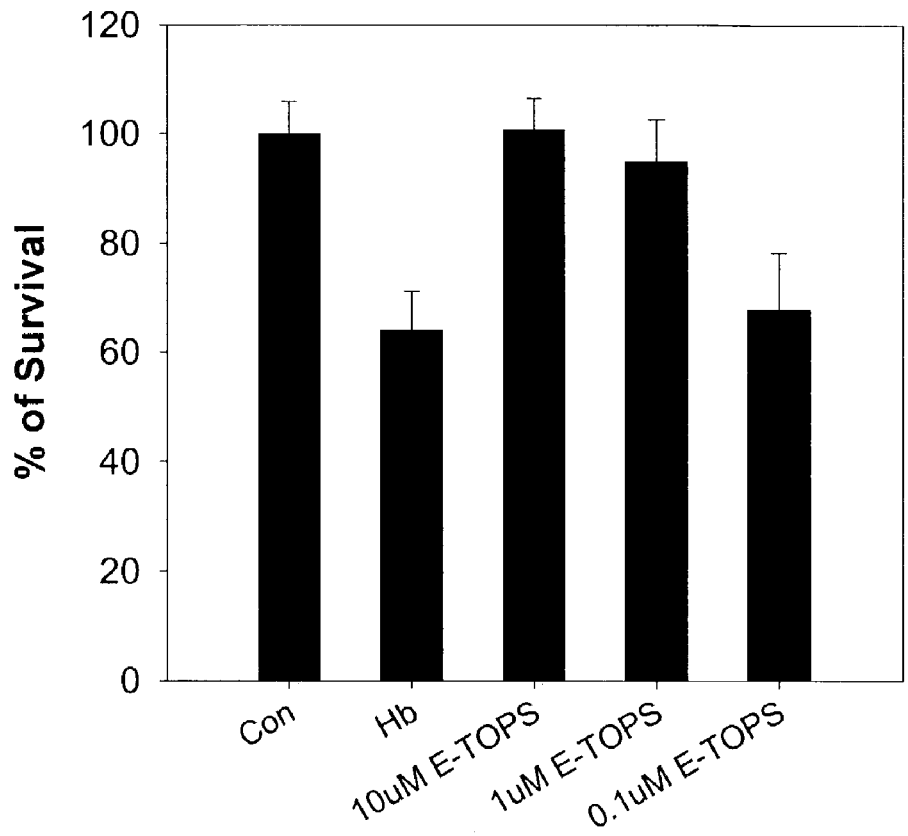
FIG. 27 shows that DE-TOPS, E-TOPS, and TOPS dose dependent inhibition of hemoglobin-induced toxicity of cortical neurons.

E-TOPS is neuroprotective in a model of hemorrhagic transformation in stroke. Primary neuronal cultures were made from forebrains of fetal rat pups (embryonic day 15). The cells were dispersed by repeated mechanical trituration in neuronal culture medium (MEM Eagle (Sigma, M4526), supplemented with glutamine (2 mM), penicilin-streptomycine (50 Units/ml-0.05 mg/ml), heat-inactivated horse serum (10%), fetal bovine serum (10%), glucose (0.5% or 28 mM). Following centrifugation (900 g; 5 min), the cells were placed onto poly-L-lysine-coated 96 well plates at a density of $5 \times 10^6$ cells/well. Hemoglobin in saline was added at 10 uM final concentration and ETOPS were added at 10 uM, 1 uM, and 0.1 uM final concentration. 24 hours after incubation neuronal viability was quantitatively determined using the colorimetric MTT assay. MTT was added to each well such that the final concentration of the dye was 0.15 mg/ml. Plates were then returned to the incubator for 1 hour at which time unincorporated MTT was removed, and the plates allowed to air dry. The purple formazan product present in viable cells was then dissolved by adding acidified isopropanol (with 0.1 N HCl in) and the absorbance intensity (540 nm) was measured using a 96 well plate reader. % Control=(Test $A_{540}$/Mean Control)×100%. FIG. 27 shows increased neuronal viability with the E-TOPS samples.

Example 10

TOPS or TOPS-ester Neuroprotection of Cortical Neurons Exposed to the Peroxynitrite Generator SIN-1

SIN-1 toxicity is studied in cultured rat cortical neurons based on the generation of peroxynitrite. The demonstration that TOPS or TOPS-ester are neuroprotective in this model, translates into nitroxide-dependent blockade of EGFR activation caused by SIN-1.

Primary neuronal cultures were made from forebrains of fetal rat pups (embryonic day 15). The cells were dispersed by repeated mechanical trituration in neuronal culture medium (MEM Eagle (Sigma, M4526), supplemented with glutamine (2 mM), penicilin-streptomycine (50 Units/ml-0.05 mg/ml), heat-inactivated horse serum (10%), fetal bovine serum (10%), glucose (0.5% or 28 mM). Following centrifugation (900 g; 5 min), the cells were placed onto poly-L-lysine-coated 96 well plates at a density of $5 \times 10^6$ cells/well. Cytotoxicity was induced in the cells according to a published procedure (Carroll et al 2000). SIN-1 (3-morpholinosydnonimine, Sigma), a PN generator, was dissolved in 50 mM phosphate (pH 5.0) just prior to use, and added to each well to give the final concentration of 1 mM. TOPS, E-TOPS or DE-TOPS were added at the indicated concentration to each culture 15 minutes prior to SIN-1. Neuronal viability was quantitatively determined using the colorimetric MTT assay. MTT was added to each well such that the final concentration of the dye was 0.15 mg/ml. Plates were then returned to the incubator for 1 hour at which time unincorporated MTT was removed, and the plates allowed to air dry. The purple formazan product present in viable cells was then dissolved by adding acidified isopropanol (with 0.1 N HCl in) and the absorbance intensity (540 nm) was measured using a 96 well plate reader. % Control=(Test $A_{540}$/Mean Control)×100%.

Figure 28:
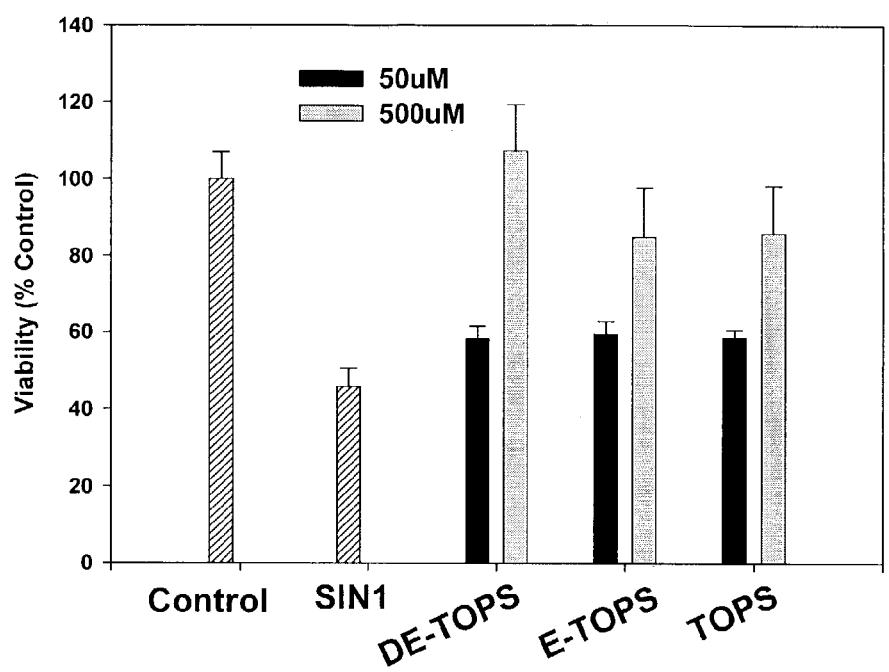
FIG. 28 shows TOPS, E-TOPS, and DE-TOPS dose dependent inhibition of peroxynitrite-induced toxicity on cortical neurons.

Referring to FIG. 28, TOPS or TOPS-esters prevented the toxicity of SIN-1 in a dose dependent manner. Neuroprotective concentrations of these compounds will prevent peroxynitrite-dependent EGFR activation by preventing the covalent dimerization of receptors and their subsequent autophosphorylation.

Example 11

Antioxidant Activity by Inhibition of Nitration

To demonstrate antioxidant activity of DE-TOPS, E-TOPS and TOPS in vitro, these compounds are compared with Tempol as the gold standard. Tempol was shown to prevent the nitration of 4-hydroxyphenylacetic acid (HPA) by peroxynitrite in vitro. In this preliminary experiment, % inhibition by Tempol, DE-TOPS, E-TOPS or TOPS of peroxynitrite-dependent nitration of HPA was measured.

Peroxynitrite was made by a procedure described previously. Solutions of 1 mM 4-hydroxyphenylacetic acid (HPA, Sigma) were made in 100 mM sodium phosphate at pH 6.5. Certain amount of TOPS, E-TOPS and DE-TOPS were added to 1 ml of HPA solution mentioned above to give a final concentration of nitroxide at 0.98, 3.91, 15.5, 62.5 and 250M. Peroxynitrite was added at a final concentration of 1 mM to start the nitration. Reactions were also carried out using inactive peroxynitrite as blank and zero nitroxide as positive control. The nitration was followed spectrophotometrically at 405 nm. The concentration of 4-hydroxy-3-nitrophenylacetate was determined spectrophotometrically ($_{430}$=4400 M$^{-1}$ cm$^{-1}$) after the pH of reaction mixtures were creased to 10–11 with NaOH.

Figure 29:
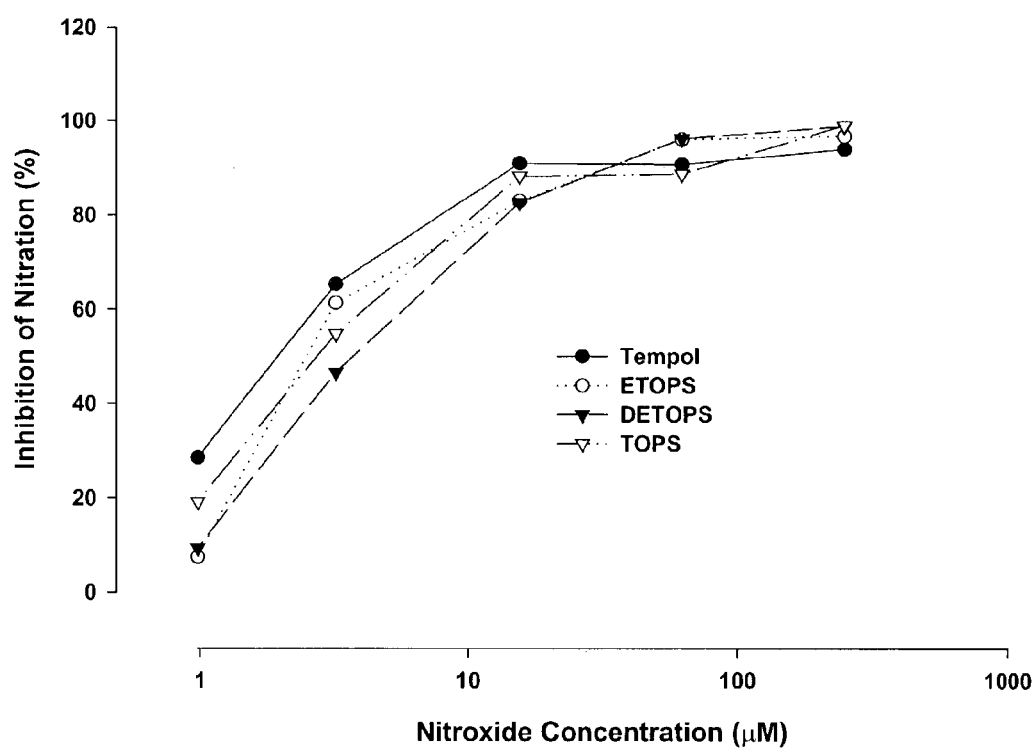
FIG. 29 shows that the nitration of hydroxy phenol acetic acid (HPA) by peroxynitrite was inhibited by TOPS, E-TOPS, and DE-TOPS in a dose-dependent manner.

Referring to FIG. 29, 40% to 60% of HPA nitration by 1 mM peroxynitrite are inhibited by the nitroxides of the invention at 3 μM. The mechanism of inhibition by nitroxides is catalytic. As peroxynitrite is suggested to be an important player in radiation-induced cellular damage, TOPS-esters has utility as a therapy for skin exposed to reactive oxygen species such as peroxynitrite.

Example 12

Cell Apoptosis Measured by Exposure to TNF-α

Figure 30:
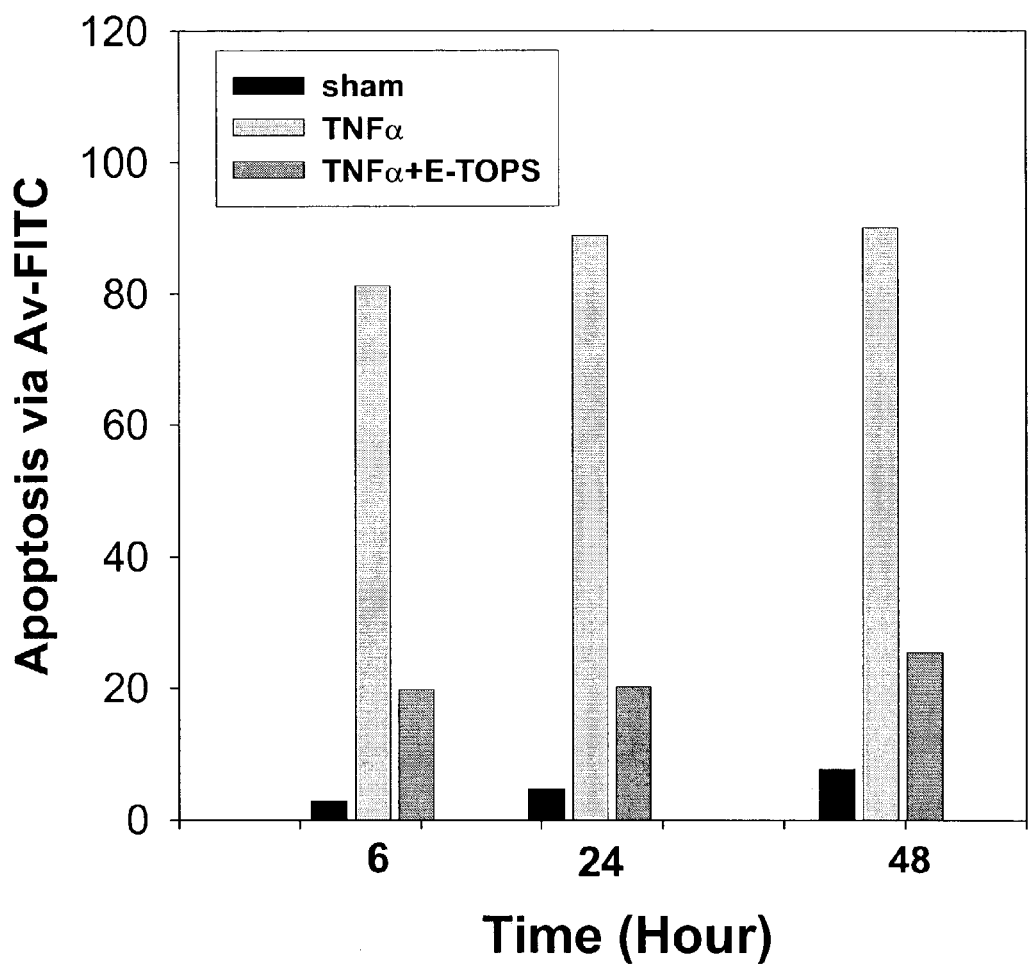
FIG. 30 shows that E-TOPS reduces apoptosis induced by tumor necrosis factor alpha (TNF-α) on Y-79 cell line at different incubation times.

The UV light induced apoptosis may be measured by a model in which apoptosis is induced by exposure to tumor necrosis factor alpha (TNF-α). As shown in FIG. 30, measurement of apoptosis severity over time for cells exposed to TNF-α plus E-TOPS is measured against a control. Cultured human Y-79 cells were maintained at pH 7.4 in culture flasks in a mixture of amphotericin/penicillin/streptomycin treated (1% v/v) RPMI 1640 media with L-glutamine and 10% fetal bovine serum in an incubator under 10%-$CO_2$/90%-air brood conditions at 37 degrees Celsius and 20% humidity. E-TOPS was prepared as a 10 mg/ml formulation. From this stock solution, 10 μl was added to 1 ml of the cell suspension solution so that the final concentration of ETOPS was 100 μg/ml of ETOPS. Human TNF-α (10 μg/1 ml) was used to prepare serial media dilutions to obtain TNF-α concentrations of 5.0 ng/ml. Cell densities and viability were determined by trypan blue exclusion assay on a Zeiss inverted microscope to ensure cell concentrations prior to cytometric assaying. After gentle mixing of the TNF-α, vial sets at the given concentrations for 6, 24, and 48 hours, the cytokine-treated cells were resuspended in PBS. The cells were resuspended in annexin V-FITC conjugate solution and incubated at room temperature in the dark for fifteen minutes. Binding buffer was then added to each of the samples to bring the cell densities up to approximately 1.0×10$^6$ cell/ml. The binding buffer was prepared by mixing the following together: 10 ml of 1M HEPES/NaOH, ph 7.4, 30 ml of 5M NaCl, 5 ml of 1M KCl, 1 ml of 1M $MgCl_2$, 1.8 ml of 1M $CaCl_2$ and 52.2 ml of DDW.

Flow cytometric methods were employed to take advantage of annexin V's reversible and calcium-dependent binding to negatively charged phosphatidylserine (PS) residues in a 1:50 annexin to PS ratio. Assay at 488 nm on a Becton-Dickinson FACStar flow cytometer was then conducted on the cells from the culture vials to determine the relative proportions of cells that were nonviable. A two dimensional x-y contour plot was used to show populations of early apoptotic events separate from late apoptotic events. Compensation was set before the cytometric trials by using an annexin-only stained population, a propidium-only stained population, and an unstained population to delimit the ceilings of detection in the respective FL-1/F1-2 quadrants. Total samplings averaged 5000 cell events counted out of sample populations averaging well over 1.0×10$^6$ cells/ml with statistics and regression analysis given for each set of sample quadrants using CellQuest software. Fluorescein stained populations alone demarcated apoptotic detection while dual counterstaining with propidium iodide indicated necrotic populations.

Example 13

Figure 31:
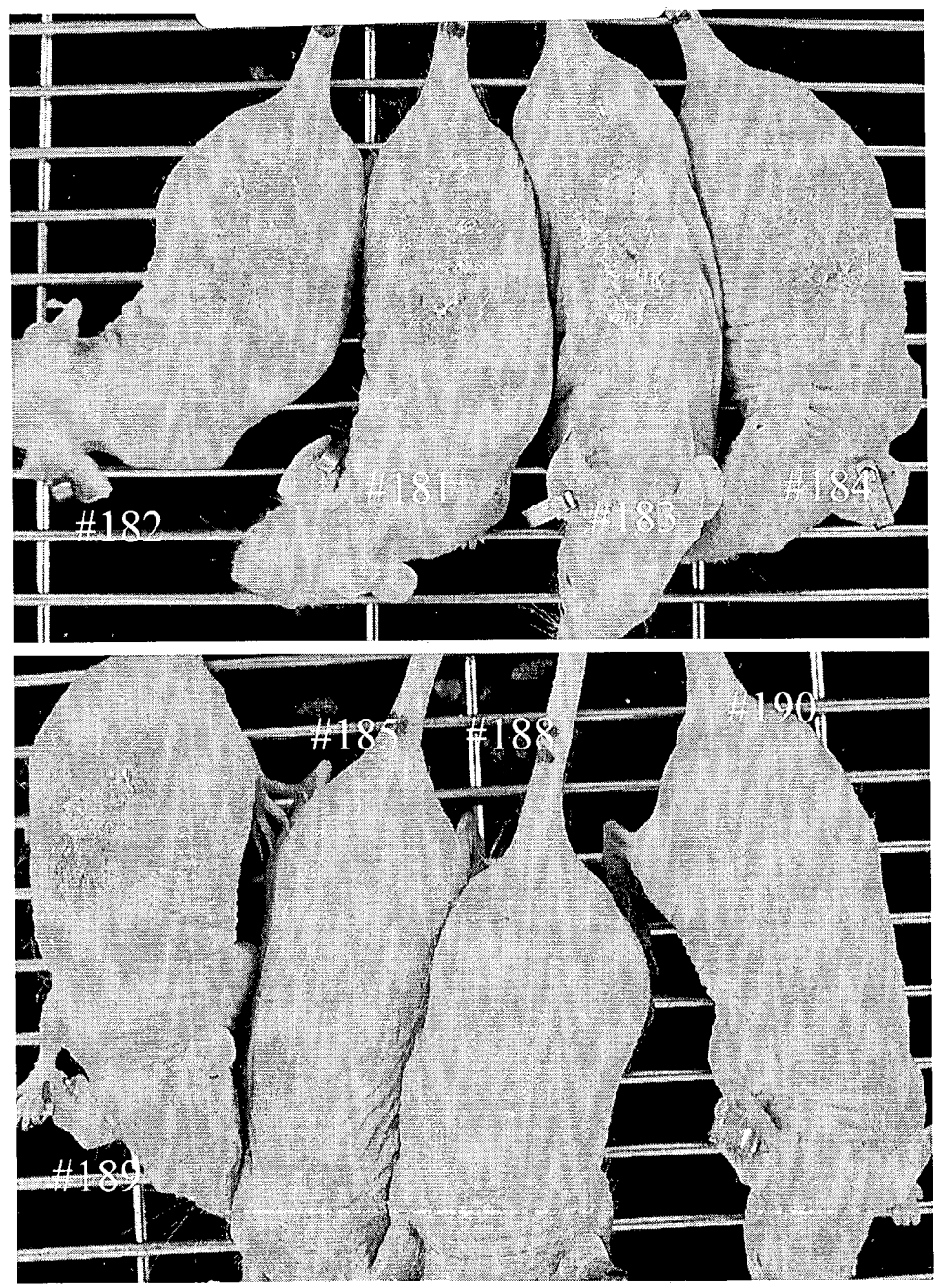
FIG. 31 shows that pre-topical application of DE-TOPS prevents UVB induced skin damage on hairless mice acutely.
Figure 32:
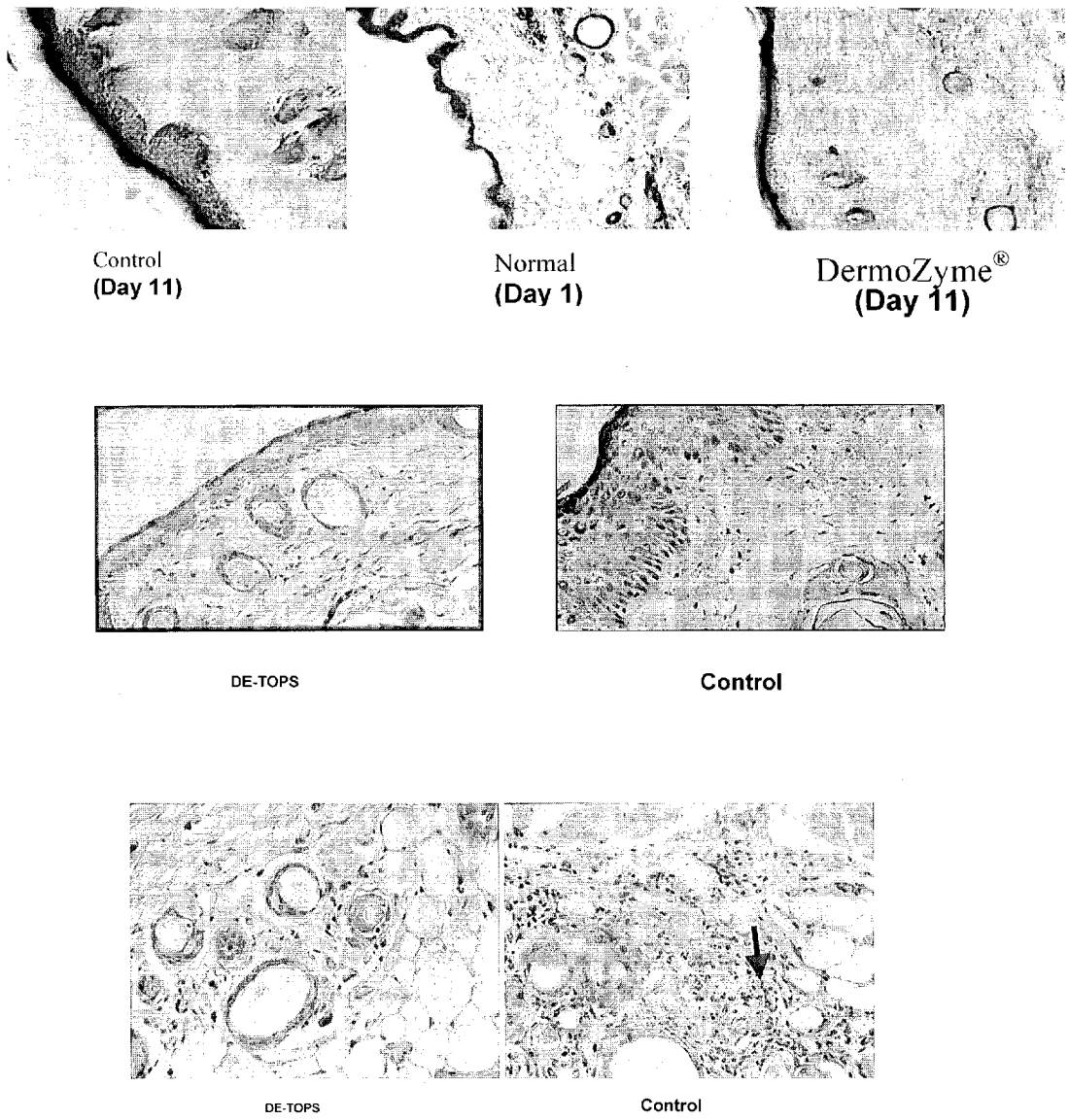
FIG. 32 shows the histopathological change of the hairless mouse skin after 11 days of UVB radiation with control or DE-TOPS applying pre-radiation
Figure 33:
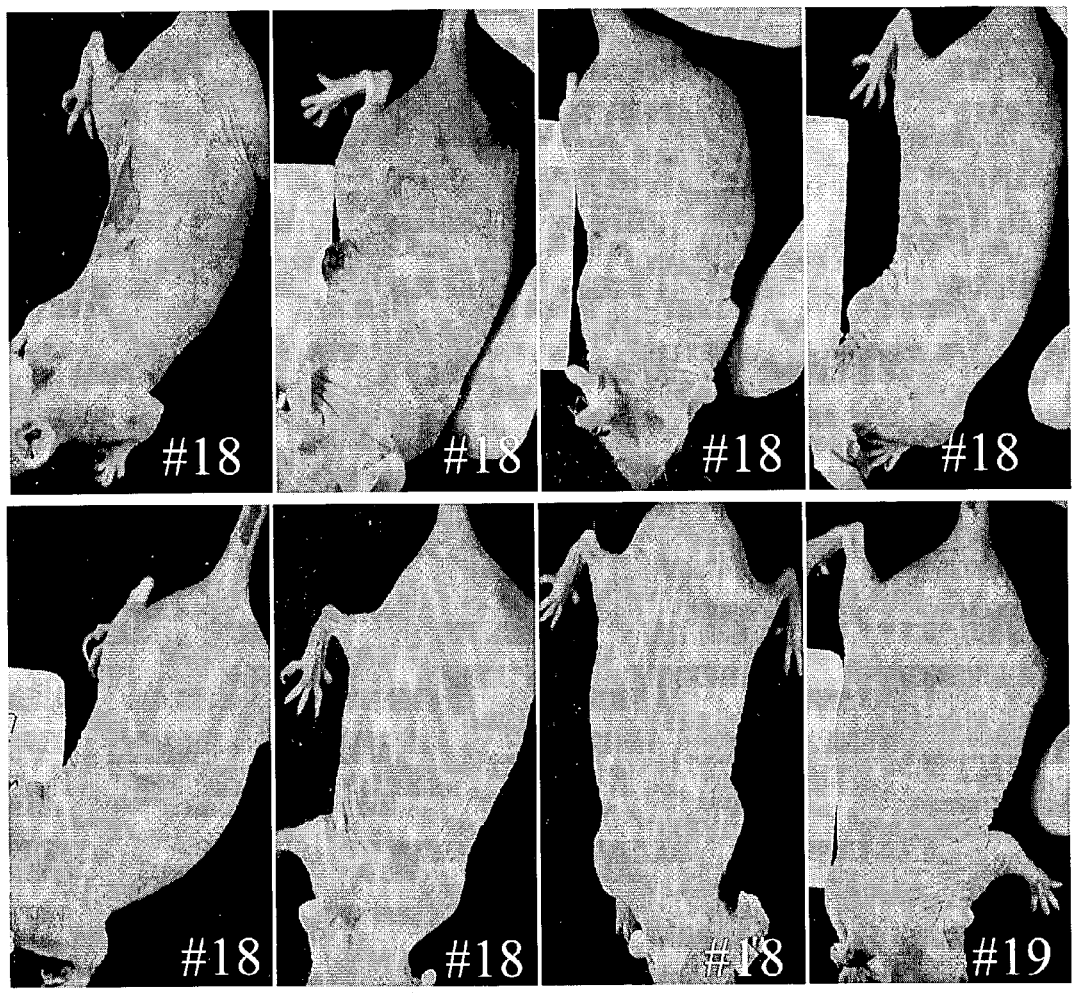
FIG. 33 shows that pre-topical application of DE-TOPS prevents UVB induced skin damage on hairless mice chronically at 4 month.

Protection Against Ultraviolet Induced Skin Damage When Applying DE-TOPS Pre Radiation Referring to FIG. 32, 11 days exposure to UVB causes significant skin thickening compared to normal mouse skin without UVB exposure. Histopathological skin sections reveal that topical application of DE-TOPS dramatically reduces skin thickening induced by UVB. Topical application was daily 10 minutes prior to UVB radiation. UVB dose was 200 mJ/cm2 during 15 minutes. UVB lamp has spectrum distribution of 290–310 nm at 80% below 310 nm at 20%. The DE-TOPS formulations are 100 mM in a petroleum base. Referring to FIG. 31, with a similar protocol, skin burn is inhibited by DE-TOPS acutely. Referring to FIG. 33, same mice were kept for 4 month, skin lesion was inhibited by DE-TOPS chronically. In this example DE-TOPS was applied 2 hour before UVB radiation.

Example 14

Figure 34:
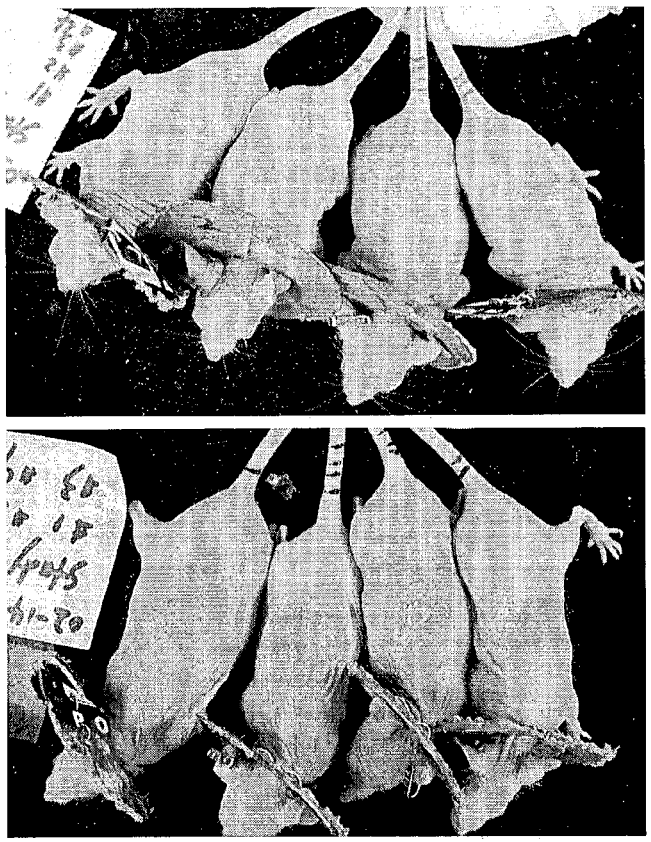
FIG. 34 shows that post-topical application of DE-TOPS prevents UVB induced skin damage on hairless mice acutely

Protection Against Ultraviolet Induced Skin Damage When Applying DE-TOPS Post Radiation Same protocol was used as in example 13 except DE-TOPS applied 15 min post radiation. The protective effect of DE-TOPS was shown in FIG. 34 and the histopathology change was shown in FIG. 35.

Example 15

Protection Against Ultraviolet Induced Skin Damage in Comparison with Tempol

Figure 36:
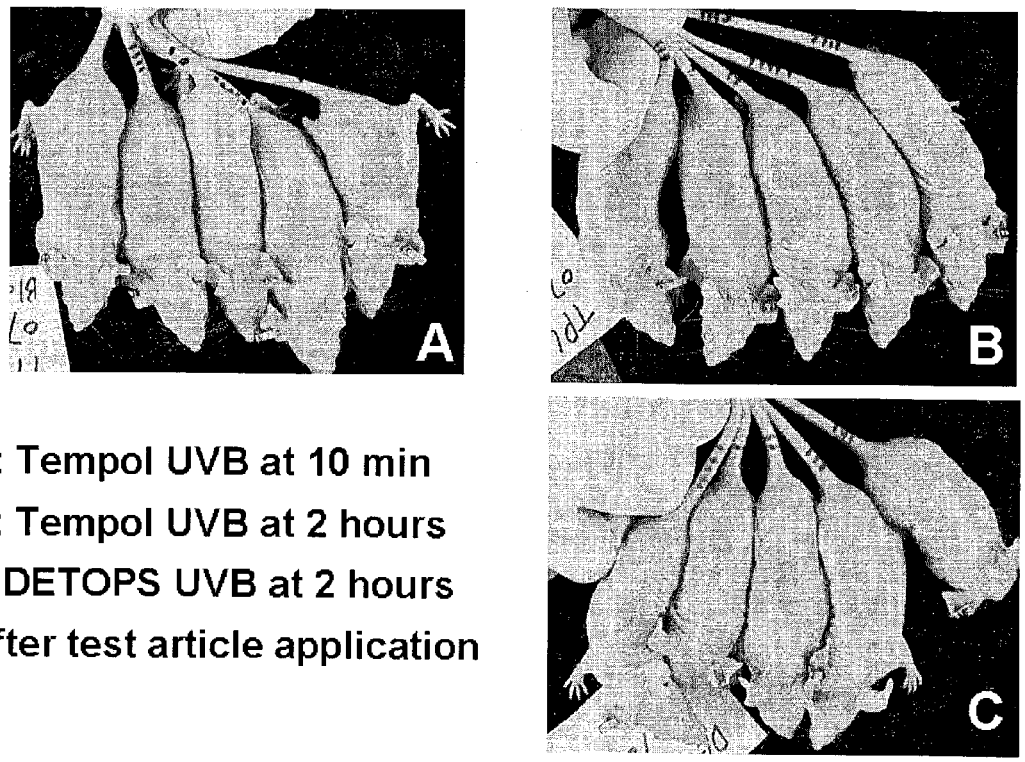

Same protocol as in example 13 was used for this study. The effect of DE-TOPS in protection of UVB induced skin damage was tested in comparison with Tempol when apply test article 10 min or 2 hour pre radiation. The results in FIG. 36 showed DE-TOPS provide longer therapeutic window that Tempol (see FIGS. 36B and C)

Example 16

Anti-wrinkle Effect of BE-TOPS in Rhino Mouse

To determine the advantage of CGN compared to commercially available topical therapies, BE-TOPS, Retin-A, and a placebo were administered to the skin of mice exposed to alternate days of UVB radiation. Treatment with Retin-A resulted in a reduction in skin wrinkling compared with control animals (See FIG. 37). Although the photo-sensitivity of Retin-A caused discoloration and flaking of the dorsal skin, cutaneous histological sections of the dorsal skin also revealed Retin-A treatment resulted in a reduction in the density of open and deep cysts.

BE-TOPS also has the advantage over Retin-A that DE-TOPS treated skin is not UVB sensitive.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A composition, comprising:
a pharmaceutically acceptable carrier; and
a compound of structural formula:

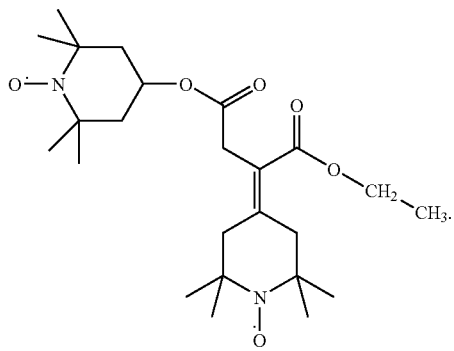

2. The composition of claim 1 further comprising: polynitroxyl albumin.

3. The composition of claim 1 further comprising: polynitroxyl starch.

4. The composition of claim 1, further comprising: a non-steroidal anti-inflammatory drug.

5. The composition of claim 1, further comprising: an antibiotic.

6. The composition of claim 1, further comprising: a copper tri-peptide.

7. The composition of claim 1, wherein the carrier is an injectable carrier.

8. The composition of claim 1, wherein the carrier is an topical carrier.

* * * * *